United States Patent
Tajima et al.

(10) Patent No.: US 11,318,162 B2
(45) Date of Patent: May 3, 2022

(54) METHOD FOR PREPARING CELL EXTRACT COMPONENT OR COMPOSITION HAVING CYTOCIDAL ACTIVITY

(71) Applicant: Medical Corporation Ichikawa Clinic, Chiba (JP)

(72) Inventors: Tomoyuki Tajima, Ichikawa (JP); Yoshifusa Kondo, Tokyo (JP)

(73) Assignee: Medical Corporation Ichikawa Clinic, Chiba (JP)

( * ) Notice: Subject to any disclaimer, the term of this patent is extended or adjusted under 35 U.S.C. 154(b) by 0 days.

(21) Appl. No.: 16/651,330

(22) PCT Filed: Oct. 5, 2018

(86) PCT No.: PCT/JP2018/037430
§ 371 (c)(1),
(2) Date: Mar. 26, 2020

(87) PCT Pub. No.: WO2019/070069
PCT Pub. Date: Apr. 11, 2019

(65) Prior Publication Data
US 2020/0222458 A1 Jul. 16, 2020

(30) Foreign Application Priority Data
Oct. 5, 2017 (JP) .............................. JP2017-194988

(51) Int. Cl.
*C12P 1/04* (2006.01)
*A61K 35/13* (2015.01)

(52) U.S. Cl.
CPC ................ *A61K 35/13* (2013.01); *C12P 1/04* (2013.01)

(58) Field of Classification Search
CPC ................................. A61K 35/13; A61P 35/00
USPC ............. 424/9.1, 9.2, 93.1, 93.7, 184.1, 520
See application file for complete search history.

(56) References Cited

U.S. PATENT DOCUMENTS

| | | |
|---|---|---|
| 4,810,495 A | 3/1989 | Tajima |
| 4,963,358 A | 10/1990 | Tajima |

FOREIGN PATENT DOCUMENTS

| | | |
|---|---|---|
| EP | 0 133 358 A2 | 2/1985 |
| JP | S59-33223 A | 2/1984 |
| JP | S60-28930 A | 2/1985 |

OTHER PUBLICATIONS

International Preliminary Report on Patentability and Written Opinion Issued in PCT/JP2018/037430; dated Apr. 8, 2020.
International Search Report issued in PCT/JP2018/037430; dated Dec. 18, 2018.

*Primary Examiner* — Patricia Duffy
(74) *Attorney, Agent, or Firm* — Studebaker & Brackett PC

(57) ABSTRACT

Provided is a method or the like for producing a composition exhibiting cytocidal activity. This method for producing a composition exhibiting cytocidal activity comprises: culturing malignant tumor-derived cells in a culture medium at least until the cell density reaches a level that does not pose a problem for transfer; replacing, after culturing, the culture medium with a physiological buffer salt solution; and recovering the physiological buffer salt solution after death of the malignant tumor-derived cells is observed morphologically in the physiological buffer salt solution.

9 Claims, 12 Drawing Sheets

(Minimum concentration of test sample exhibiting 0% survival rate for HRC23 is expressed as 1.)

METHOD FOR PREPARING CELL EXTRACT COMPONENT OR COMPOSITION HAVING CYTOCIDAL ACTIVITY

TECHNICAL FIELD

The present invention relates to a method for producing a composition having cytocidal activity, a method for preparing a cell extract component having cytocidal activity, and the like.

BACKGROUND ART

When cells are cultured, many established cell lines can grow indefinitely if they are dispersed with trypsin or the like at the time when the cells have grown up and have covered fully the culture vessel surface, diluted in fresh medium, and transferred to another culture vessel for culturing. This is called passage, and if culturing is continued without passage, the cells die.

Patent Literature 1 discloses a malignant tumor cell growth inhibitor obtained by removing malignant tumor cells from a medium after culturing malignant tumor cells. However, what was obtained by removing malignant tumor cells from the medium was a composition containing extremely miscellaneous substances, and the isolation of substances having antineoplastic activity from such a composition was greatly difficult and considered to be virtually impossible.

CITATION LIST

Patent Literatures

Patent Literature 1: Japanese Patent Application Publication No. Sho 59-33223

SUMMARY OF INVENTION

To date, various therapeutic agents have been researched and developed for the purpose of cancer treatment. However, since conventional anticancer agents often have strong side effects and fail to achieve sufficient effects, there is still a need for further drug development.

An aspect of the present invention makes it possible to provide a method for producing, from cultured cells, a composition which can be used as a novel anticancer agent, or a composition which can be used to obtain a substance useful as a novel anticancer agent.

In addition, an aspect of the present invention can provide a method which makes it possible to obtain a cell extract component having cytocidal activity.

The present inventors have made earnest studies and have newly found that the phenomenon of cell death in the case of continuing cell culture without passage appears even if the cells are replenished with sufficient nutrients and energy sources by medium replacement at the time when growth suppression occurs due to overpopulation after the cells cover fully the culture vessel surface to further grow.

In addition, the present inventors have newly found that malignant tumor-derived cells produce a substance which causes themselves to die even in the case where the cells are cultured in a culture medium at least until a cell density reaches a level that does not pose an obstacle for passage, and then the culture medium is replaced with a physiological buffer salt solution (containing no nutrient and/or energy source). This is a finding indicating that cells produce a substance having cytocidal activity from only substances present in the cells, and cause themselves to die. Such finding has not been reported or suggested so far, and it is utterly unexpected that a physiological buffer salt solution can be used to obtain a component having cytocidal activity extracted from malignant tumor-derived cells.

An embodiment of the present invention relates to the following.

[1] A method for producing a composition having cytocidal activity, the method comprising:
culturing malignant tumor-derived cells in a culture medium at least until a cell density reaches a level that does not pose an obstacle for passage;
replacing, after the culturing, the culture medium with a physiological buffer salt solution; and
recovering the physiological buffer salt solution after the time at which death of the malignant tumor-derived cells is observed in the physiological buffer salt solution in morphological aspect of said cells.

[2] The production method according to [1] described above, wherein the physiological buffer salt solution is glucose-free.

[3] The production method according to [1] or [2] described above, wherein the physiological buffer salt solution is selected from the group consisting of Hanks' balanced salt solution, Earle's balanced salt solution, and phosphate buffered saline.

[4] The production method according to any one of [1] to [3] described above, further comprising
obtaining a dried product containing a fraction with a molecular weight of 1 kDa or less in the recovered physiological buffer salt solution, and
dissolving the dried product in a medium to obtain a solution and removing a salt, a nucleic acid, and a protein from the resulting solution.

[5] The production method according to any one of [1] to [4] described above, wherein the composition having cytocidal activity contains a cell extract component derived from the malignant tumor-derived cells.

[6] A method for preparing a cell extract component derived from malignant tumor-derived cells, the method comprising:
culturing malignant tumor-derived cells in a culture medium at least until a cell density reaches a level that does not pose an obstacle for passage;
replacing, after the culturing, the culture medium with a physiological buffer salt solution;
recovering the physiological buffer salt solution after the time at which death of the malignant tumor-derived cells is observed in the physiological buffer salt solution in morphological aspect of said cells;
obtaining a dried product containing a fraction with a molecular weight of 1 kDa or less in the recovered physiological buffer salt solution;
extracting the dried product using a solvent containing an alcohol having 1 to 3 carbon atoms, and drying a resultant solution;
dissolving a dried product of the resultant solution in water to obtain an aqueous solution, adding a non-polar organic solvent to the aqueous solution to form an aqueous layer and an organic layer, and extracting the aqueous layer; and
separating a cell extract component derived from the malignant tumor-derived cells from the aqueous layer by chromatography, wherein
the cell extract component has cytocidal activity.

[7] The preparation method according to [6] described above, wherein the chromatography includes gel filtration chromatography and/or cation exchange chromatography.
[8] The production method or the preparation method according to any one of [1] to [7] described above, wherein the malignant tumor-derived cells are not genetically engineered and are cultured without adding a physiologically active substance other than a culture solution.
[9] A composition having cytocidal activity which is obtained by the production method according to any one of [1] to [5] and [8] described above.
[10] A cell extract component derived from malignant tumor-derived cells which is obtained by the preparation method according to [6] or [7] described above.
[11] A pharmaceutical composition for treating cancer comprising the composition having cytocidal activity obtained by the production method according to any one of [1] to [5] and [8] described above.
[12] A pharmaceutical composition for treating cancer comprising, as an active ingredient, the cell extract component derived from the malignant tumor-derived cells obtained by the preparation method according to [6] or [7] described above.
[13] Use of the composition having cytocidal activity obtained by the production method according to any one of [1] to [5] and [8] described above for the production of a medicament for treating cancer.
[14] Use of the cell extract component derived from the malignant tumor-derived cells obtained by the preparation method according to [6] or [7] described above for the production of a medicament for treating cancer.

An aspect of the present invention makes it possible to inexpensively, conveniently, and/or in a short period of time, produce a composition which can be used as a novel anticancer agent, or a composition which can be used to obtain a substance useful as a novel anticancer agent.

An aspect of the present invention makes it possible to obtain a cell extract component having cytocidal activity inexpensively, conveniently, and/or in a short period of time. The cell extract having cytocidal activity may be effective against various cancers.

DESCRIPTION OF EMBODIMENTS

Figure 1:
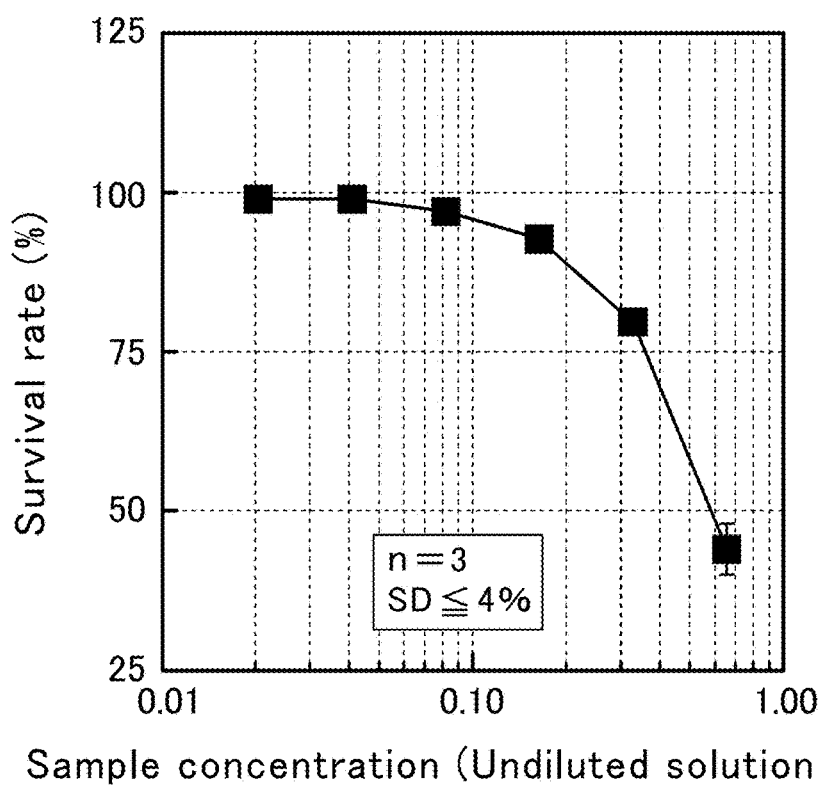
FIG. 1 is a semi-log graph illustrating the average value and standard deviation of HRC23 cell survival rate measured by MTT (3-(4,5-dimethylthiazol-2-yl)-2,5-diphenyltetrazolium bromide) assay (a colorimetric assay for assessing cell metabolic activity) in a serial dilution series of test samples prepared from HRC23 using a serum-containing medium (Eagle's MEM with 10% FBS). The horizontal axis represents the concentration of the test sample (undiluted solution mL/mL) on a common logarithmic scale.

Hereinafter, the present invention is described in detail.

An embodiment of the present invention is a method for producing a composition having cytocidal activity, the method comprising:

culturing malignant tumor-derived cells in a culture medium at least until a cell density reaches a level that does not pose an obstacle for passage;

replacing, after the culturing, the culture medium with a physiological buffer salt solution; and recovering the physiological buffer salt solution after the time at which death of the malignant tumor-derived cells is observed in the physiological buffer salt solution in morphological aspect of said cells.

In the present specification, the "malignant tumor-derived cell" means a cultured cell (primary cultured cell) obtained from a malignant tumor or a malignant tumor-derived established cell line. Established cultured cell lines have a characteristic in common that they can be cultured indefinitely if subjected to passage, and die even in a fresh medium without passage. From this, it is considered that a cell-derived substance having cytocidal activity is involved in the "natural cell death" (necrosis) to kill the cells. Therefore, all established cell lines are considered to be a raw material for producing substances having such cytocidal activity.

The "malignant tumor" is generally referred to as cancer and is used in a broad sense including carcinoma, sarcoma, and hematologic malignancy (hematopoietic tumor).

For example, whether epithelial or non-epithelial, the "malignant tumor-derived cells" may be derived from cancer such as lung cancer, gastric cancer, esophageal cancer, liver cancer, biliary tract cancer, pancreatic cancer, large bowel cancer, renal cancer, bladder cancer, prostatic cancer, testicular cancer, uterine cancer, ovarian cancer, breast cancer, skin cancer, laryngeal cancer, colorectal cancer, melanoma, thyroid cancer, fibrosarcoma, dermatofibrosarcoma, uterine sarcoma, liposarcoma, myosarcoma, hemangiosarcoma, Kaposi's sarcoma, lymphangiosarcoma, osteosarcoma, leukemia, lymphoma, and myeloma. These cancers may be derived from humans or may be derived from mammals (except for humans) such as mice.

In addition, whether epithelial or non-epithelial, the "malignant tumor-derived cells" are not limited to adenocarcinoma, squamous cell carcinoma, small cell carcinoma, and large cell carcinoma, and may be derived from any tissue type including sarcoma.

In an embodiment of the present invention, the "malignant tumor-derived cells" may be ones which are not genetically engineered and are cultured without adding a physiologically active substance other than a culture solution.

In the production method of the present invention, the "culturing malignant tumor-derived cells in a culture medium at least until a cell density reaches a level that does not pose an obstacle for passage" can be appropriately carried out based on known techniques.

For example, the culturing at least until a cell density reaches a level that does not pose an obstacle for passage can be culturing cells to a confluent state, or culturing cells to a fully confluent state. In addition, the culturing at least until a cell density reaches a level that does not pose an obstacle for passage is not limited to the above, and may be culturing cells to a 60 to 100% confluent state, preferably a 70 to 100% confluent state, may be culturing cells until the adherent surface of the culture vessel is completely covered or until the adherent surface of the culture vessel is covered at least about 80% if the cells are adherent cells, or may be culturing cells until the liquid surface of the culture medium is completely covered or until the liquid surface of the culture medium is covered at least about 80% if the cells are floating cells. From the viewpoint of the efficiency of producing a cell extract component having cytocidal activity, it is more preferable to culture cells to a 80 to 100% confluent state, it is further preferable to culture cells to a 90 to 100% confluent state, and it is even more preferable to culture cells to a confluent state or a fully confluent state. Whether or not at least the density of cells has reached a level that does not pose an obstacle for passage can be appropriately determined based on the ordinary knowledge of those skilled in the art.

In the production method of the present invention, the culture medium used may be one which is suitable for the malignant tumor-derived cells to be used. For example, the culture medium includes Eagle's MEM, Dulbecco's modified MEM, RPMI 1640, HAM F-12, a completely synthetic medium which does not require FBS, and the like. In addition, if necessary, these culture media may be added with vitamins, coenzymes, amino acids, metal ions, sugars, cell growth factors, interleukins, cytokines, serum, serum-derived components, antibiotics, and the like.

In the production method of the present invention, the malignant tumor-derived cells used may already be subjected to passage, and the passage can be conducted based on the ordinary knowledge of those skilled in the art.

In the production method of the present invention, the "replacing the culture medium with a physiological buffer salt solution" is, for example, removing the culture medium from the culture vessel such as a culture flask and then adding a physiological buffer salt solution to the culture vessel.

The physiological buffer salt solution is not particularly limited to, but includes, for example, Hanks' balanced salt solution (HBSS), Earle's balanced salt solution, phosphate buffered saline (PBS), Ringer's balanced salt solution, Simms' balanced salt solution, Tyrode's balanced salt solution, Gey's balanced salt solution, Puck's balanced salt solution, Eagle's balanced salt solution, and the like. Preferably, the physiological buffer salt solution is glucose-free. An additional component such as an antibiotic may or may not be added to the physiological buffer salt solution.

In an embodiment of the present invention, the physiological buffer salt solution is Hanks' balanced salt solution, Earle's balanced salt solution, or phosphate buffered saline, and is preferably glucose-free. More preferably, the physiological buffer salt solution is glucose-free Hanks' balanced salt solution (HBSS−).

In the production method of the present invention, the "recovering the physiological buffer salt solution after the time at which death of the malignant tumor-derived cells is observed in the physiological buffer salt solution in morphological aspect of said cells" is, for example, recovering the physiological buffer salt solution after the time at which death of the malignant tumor-derived cells can be confirmed in morphological aspect of the cells by microscopic observation, MTT method, or the like. The observation or confirmation of morphological cell death of the malignant tumor-derived cells can be appropriately determined based on the ordinary knowledge of those skilled in the art depending on the type of malignant tumor-derived cells used. For example, if cells are seen peeled off when the flask is lightly hit or if cells (fragments) are seen suspended with the naked eye, it is recognized that morphological cell death of the malignant tumor-derived cells can be observed or confirmed.

The "after the time at which death of the malignant tumor-derived cells is observed in morphological aspect of said cells" may vary depending on the type of malignant tumor-derived cells used and the conditions of cell culture, and may be, for example, three to seven days after the day when a culture medium is replaced with a physiological buffer salt solution. Even if dead cell fragments are contained after recovery, they are stable for 1 month at 4° C. under aseptic conditions at the level during culture.

In addition, it is preferable to centrifuge a physiological buffer salt solution after recovery, and to collect a resultant supernatant. The conditions for centrifugation may be, but are not limited to, 1,000 to 17,000×g for 10 to 20 minutes at 4° C. to room temperature (for example, 25° C.). In addition, it is preferable to filter the supernatant using a membrane filter such as a 0.1 μm membrane filter, and to collect a filtrate.

In the production method of the present invention, it is possible to appropriately select the conditions for culturing malignant tumor-derived cells in a physiological buffer salt solution after the time at which death of the malignant tumor-derived cells is observed in morphological aspect of the cells and until recovering the physiological buffer salt solution. Basically, in the case of a physiological buffer salt solution designed to be an open system such as HBSS−, incubation is carried out at 36° C. to 37° C. in an incubator or a temperature-controlled room in a closed system which does not allow water evaporated in the atmosphere to escape. Alternatively, malignant tumor-derived cells may be incubated in a physiological buffer salt solution under the same conditions as the ordinary culture conditions. For example, the same conditions as the ordinary culture conditions are, but not limited to, a temperature range of 30° C. to 38° C., preferably 35° C. to 37° C., a humidity range of 70 to 100%, preferably 90 to 100%, and a carbon dioxide range of 2 to 8%, preferably 4 to 6%. In addition, a physiological buffer salt solution which requires pH control with carbon dioxide gas can be used as well, with a reduced $NaHCO_3$ content.

The production method of the present invention may further include obtaining a dried product containing a fraction with a molecular weight of 1 kDa or less in the recovered physiological buffer salt solution. The fraction with a molecular weight of 1 kDa or less can be obtained by a known means such as ultrafiltration using a commercially available membrane filter or the like. In addition, the dried product containing a fraction with a molecular weight of 1 kDa or less can be obtained by a known means such as vacuum drying.

The production method of the present invention may further include dissolving the thus obtained dried product in a medium to obtain a solution and removing a salt, a nucleic acid, and a protein from the resulting solution. Specifically, the dissolving the dried product in a medium to obtain a solution and removing a salt, a nucleic acid, and a protein from the resulting solution can be carried out by, but not limited to, the following steps.

(1) The step of extracting the dried product using a solvent containing an alcohol having 1 to 3 carbon atoms, and drying a resultant solution, and the step of dissolving a dried product of the resultant solution in water to obtain an aqueous solution and adding an organic solvent to the aqueous solution or adding a dried product of the resultant solution to a water-added organic solvent to form an aqueous layer and an organic layer, and extracting the aqueous layer.

Here, the solvent containing an alcohol having 1 to 3 carbon atoms is specifically a solvent containing methanol, ethanol, n-propyl alcohol, or isopropyl alcohol. The solvent containing an alcohol having 1 to 3 carbon atoms may be a liquid mixture with e.g. an alcohol or an organic solvent such as chloroform.

In addition, the organic solvent is not particularly limited as long as it is sufficient to form an aqueous layer and an organic layer, and examples thereof usable include non-polar organic solvents, specifically, chloroform, a liquid mixture of chloroform and ethyl acetate, and the like.

The "extracting the dried product using a solvent containing an alcohol having 1 to 3 carbon atoms" means, for example, adding a solvent containing an alcohol having 1 to 3 carbon atoms to a dried product, followed by centrifugation at 1000 to 2000×g for 5 to 10 minutes to obtain a supernatant.

(2) The step of adding the dried product to a water-added organic solvent to form an aqueous layer and an organic layer, and extracting the aqueous layer, and the step of removing a salt and the like from the aqueous layer by chromatography.

Here, the organic solvent is not particularly limited as long as it is sufficient to form an aqueous layer and an organic layer. Although gel filtration chromatography is preferable for removing a salt and the like by chromatography, it is not limited thereto.

The composition having cytocidal activity obtained by the production method of the present invention contains a cell extract component having cytocidal activity derived from malignant tumor-derived cells. As demonstrated in Examples to be described later, the cell extract component having cytocidal activity is effective against various cancers, and even against mouse Lewis lung carcinoma, which is considered to have resistance to various anticancer agents.

A glucose-free physiological buffer salt solution is a medium which has no nutrients and no energy sources for cells. Therefore, it has been revealed that the cell extract component having cytocidal activity derived from malignant tumor-derived cells, which is contained in the composition having cytocidal activity obtained by the production method of the present invention, is produced by the cells using only the substances present in the cells as materials.

Serum-containing media and serum-free media used for culturing cells contain various components suitable for culturing cells. Thus, it is extremely difficult to isolate and purify a cell extract component having cytocidal activity derived from malignant tumor-derived cells from serum-containing media and serum-free media. On the other hand, isolation and purification of a cell extract component having cytocidal activity derived from malignant tumor-derived cells from a physiological buffer salt solution is easier than the isolation and purification from serum-containing media and serum-free media. Therefore, the production method of the present invention can make it possible to obtain a cell extract component having cytocidal activity inexpensively, conveniently, and/or in a short period of time. In particular, consider the case of using a glucose-free physiological buffer salt solution. The composition having cytocidal activity obtained by the production method of the present invention becomes a system which does not contain an energy source, making it possible to reduce the amount of lactic acid produced and to prevent a decrease in pH. In addition, since lactic acid is soluble in an organic solvent such as ethanol, reducing the amount of lactic acid produced makes it possible to suppress the influence on purification.

An embodiment of the present invention is a method for preparing a cell extract component derived from malignant tumor-derived cells, the method comprising:

culturing malignant tumor-derived cells in a culture medium at least until a cell density reaches a level that does not pose an obstacle for passage;

replacing, after the culturing, the culture medium with a physiological buffer salt solution;

recovering the physiological buffer salt solution after the time at which death of the malignant tumor-derived cells is observed in the physiological buffer salt solution in morphological aspect of said cells;

obtaining a dried product containing a fraction with a molecular weight of 1 kDa or less in the recovered physiological buffer salt solution;

extracting the dried product using a solvent containing an alcohol having 1 to 3 carbon atoms, and drying a resultant solution;

dissolving a dried product of the resultant solution in water to obtain an aqueous solution, adding a non-polar organic solvent to the aqueous solution to form an aqueous layer and an organic layer, and extracting the aqueous layer; and separating a cell extract component derived from the malignant tumor-derived cells from the aqueous layer by chromatography, wherein the cell extract component has cytocidal activity.

In the preparation method of the present invention, the "culturing malignant tumor-derived cells in a culture medium at least until a cell density reaches a level that does not pose an obstacle for passage," the "replacing the culture medium with a physiological buffer salt solution," the "recovering the physiological buffer salt solution after the time at which death of the malignant tumor-derived cells is observed in the physiological buffer salt solution in morphological aspect of said cells," and the "obtaining a dried product containing a fraction with a molecular weight of 1 kDa or less in the recovered physiological buffer salt solution" are the same as those in the above-described method for producing a composition having cytocidal activity.

In the preparation method of the present invention, the "extracting the dried product using a solvent containing an alcohol having 1 to 3 carbon atoms, and drying a resultant solution" can be carried out by an ordinary extraction operation.

Here, the solvent containing an alcohol having 1 to 3 carbon atoms is specifically a solvent containing methanol, ethanol, n-propyl alcohol, or isopropyl alcohol. The solvent containing an alcohol having 1 to 3 carbon atoms may be a liquid mixture with e.g. an alcohol or an organic solvent such as chloroform.

The "extracting the dried product using a solvent containing an alcohol having 1 to 3 carbon atoms" means, for example, adding a solvent containing an alcohol having 1 to 3 carbon atoms to a dried product, followed by centrifugation at 1000 to 2000×g for 5 to 10 minutes to obtain a supernatant.

In the preparation method of the present invention, the "dissolving a dried product of the solution in water to obtain an aqueous solution, adding a non-polar organic solvent to the aqueous solution to form an aqueous layer and an organic layer, and extracting the aqueous layer" can be carried out by an ordinary extraction operation.

The non-polar organic solvent is not particularly limited as long as it is sufficient to form an aqueous layer and an organic layer, and examples thereof usable include chloroform, a liquid mixture of chloroform and ethyl acetate, and the like.

In the preparation method of the present invention, the "separating a cell extract component derived from the malignant tumor-derived cells from the aqueous layer by chromatography" can be carried out by a known chromatography technique. Preferably, gel filtration chromatography and/or cation exchange chromatography is used to separate cell extract components having cytocidal activity derived from malignant tumor-derived cells.

Here, gel filtration chromatography and cation exchange chromatography can be appropriately carried out using commercially available apparatuses, carriers, and columns. The cation exchange chromatography may elute the target substance by the gradient method (concentration gradient method), or may elute the target substance by the isocratic method (isocratic elution method).

In cation exchange chromatography, it is preferable to use a strong cation exchange column.

An embodiment of the present invention relates to a composition having cytocidal activity which is obtained by the above-described production method of the present invention.

An embodiment of the present invention relates to a cell extract component derived from malignant tumor-derived cells which is obtained by the above-described preparation method of the present invention.

The composition having cytocidal activity, which is obtained by the above-described production method of the present invention, is derived from malignant tumor-derived cells, and it is impossible or impractical to directly identify said composition with the structure or characteristics thereof. Regarding the cell extract component derived from malignant tumor-derived cells obtained by the preparation method of the present invention, the structural identification of that substance requires a large quantity of pure product samples and very expensive measuring equipment. In addition, it is necessary to examine various properties of the substance such as stability and then to repeat a great number of trials and errors, which requires a great deal of time and money. Therefore, the structure identification is nearly impractical.

An embodiment of the present invention relates to a pharmaceutical composition for treating cancer comprising the composition having cytocidal activity obtained by the above-described production method of the present invention.

An embodiment of the present invention relates to a pharmaceutical composition for treating cancer comprising, as an active ingredient, the cell extract component derived from the malignant tumor-derived cells obtained by the above-described preparation method of the present invention.

An embodiment of the present invention relates to use of the composition having cytocidal activity obtained by the above-described production method of the present invention for the production of a medicament for treating cancer.

An embodiment of the present invention relates to use of the cell extract component derived from the malignant tumor-derived cells obtained by the above-described preparation method of the present invention for the production of a medicament for treating cancer.

Cancers which can be treated by the pharmaceutical composition for treating cancer or the medicament for treating cancer of the present invention are not limited by the types of malignant tumor-derived cells used in the above-described production method or preparation method of the present invention. Specifically, the pharmaceutical composition for treating cancer or the medicament for treating cancer of the present invention can be effective against the same type of cancer as or different types of cancer from malignant tumor-derived cells used in the above-described production method or preparation method of the present invention.

In addition, the pharmaceutical composition for treating cancer or the medicament for treating cancer of the present invention can be effective in any of carcinoma, sarcoma, and hematologic malignancy (hematopoietic tumor). Cancers which can be treated by the pharmaceutical composition for treating cancer or the medicament for treating cancer of the present invention are not limited to adenocarcinoma, squamous cell carcinoma, small cell carcinoma, and large cell carcinoma, and may be derived from any tissue type including sarcoma. For example, cancers which can be treated by the pharmaceutical composition for treating cancer or the medicament for treating cancer of the present invention include, but are not limited to, lung cancer, gastric cancer, esophageal cancer, liver cancer, biliary tract cancer, pancreatic cancer, large bowel cancer, renal cancer, bladder cancer, prostatic cancer, testicular cancer, uterine cancer, ovarian cancer, breast cancer, skin cancer, laryngeal cancer, colorectal cancer, melanoma, thyroid cancer, fibrosarcoma, skin fibrosarcoma, uterine sarcoma, liposarcoma, myosarcoma, hemangiosarcoma, Kaposi's sarcoma, lymphangiosarcoma, osteosarcoma, leukemia, lymphoma, myeloma, and the like.

The pharmaceutical composition for treating cancer or the medicament for treating cancer of the present invention may contain additives which can be used in medicaments, such as pharmaceutically acceptable carriers, diluents, excipients, and stabilizers. These additives can be appropriately selected based on the common technical knowledge of those skilled in the art.

The cell extract component having cytocidal activity derived from malignant tumor-derived cells, which is obtained by the above-described preparation method of the present invention, is expected to be a water-soluble low molecular weight compound having a molecular weight of 1 kDa or less, and thus is expected to be used in various forms as a medicament. For example, the pharmaceutical composition for treating cancer or the medicament for treating cancer of the present invention can be administered to a subject orally or parenterally such as by injection.

EXAMPLES

Hereinafter, the present invention is described in more detail with reference to specific examples, but the scope of the present invention is not limited to these examples.
[Malignant Tumor-Derived Established Cell Lines Used]
(1) Human Renal Cancer-Derived Cell Line: HRC23

HRC23 is one established as a cell line by transplantation of human renal cell carcinoma in nude mice. For passage, phenol red- and antibiotic-free Eagle's MEM (Nissui Pharmaceutical Co., Ltd.) supplemented with 10% FBS was used, and for cell detachment, 0.1% trypsin and 0.01% EDTA were used. In addition, cloning was carried out as needed. The culturing was carried out at 37° C. under 5% $CO_2$.
(2) Mouse Lewis Lung Carcinoma-Derived Cell Line A cell line distributed by RIKEN was used (RCB0558: LLC). For passage, Eagle's MEM supplemented with 10% FBS was used, and for cell detachment, 0.1% trypsin and 0.01% EDTA were used. The culturing was carried out at 37° C. under 5% $CO_2$. The cells are highly metastatic and resistant to various anticancer agents, and are cells obtained by culturing ones which have been passaged in vivo (Bertram J S, Janik P., Cancer Lett. 1980 November, 11(1), p. 63-73).
(3) Other Human Malignant Tumor-Derived Cell Lines Four types of cell lines derived from human malignant tumors were used. All of these cells were obtained from the National Institute for Biomedical Innovation, the Japanese Collection of Research Bioresources Cell Bank. For passage and assay, the indicated media and cell detachment enzymes were used. The culturing was carried out at 37° C. under 5% $CO_2$.

Table 1 presents the types of cells used.

TABLE 1

| Cell Name | Derived From | Tissue Type | Culture Medium (+10% FBS) |
|---|---|---|---|
| HRC23 | Human Renal Cell Carcinoma | Adenocarcinoma | Eagle's MEM |
| MKN74 (JCRB0255) | Human Gastric Cancer | Adenocarcinoma | RPMI1640 |
| LK-2 (JCRB0829) | Human Lung Cancer | Squamous Cell Carcinoma | RPMI1640 |
| VMRC-JCP (JCRB0103) | Human Lung Cancer | Squamous Cell Carcinoma | RPMI1640 |
| SKN (JCRB0173) | Human Uterine Sarcoma | Leiomyosarcoma | Eagle's MEM |
| LLC (RCB0558) | Mouse Lewis Lung Carcinoma | Medullary Carcinoma | Eagle's MEM |

Pathologically, malignant tumors are roughly classified into epithelial and non-epithelial ones, and many of them are epithelial. In Table 1, SKN is non-epithelial, and the others are epithelial, where LLC is known as a mouse-derived epithelial malignant tumor cell which is different in species and resistant to various anticancer agents. In addition, representative cells were selected in terms of tissue type.

Example 1: Preparation of Undiluted Solution Sample (1) Undiluted Solution Sample Prepared Using Serum-Containing Medium HRC23 was cultured in Eagle's MEM with 10% FBS in the same manner as that of passage. The Eagle's MEM used was an antibiotic- and phenol red-free medium. HRC23 was cultured in a flask until cell growth reached a confluent state, and was further cultured to overgrowth (overpopulation). Then, the medium was finally replaced with Eagle's MEM with 10% FBS as described above, followed by incubation at 37° C. under 5% $CO_2$. After nine days, death of the cells was observed in morphological aspect of HRC23. After that, the medium was recovered and centrifuged at $3 \times 10^3 \times g$ for 10 minutes to obtain a supernatant. This supernatant was filtered with a 0.1 μm membrane filter (Millex® VV, Merck & Co., Inc. (Millipore)), and the filtrate was stored aseptically at 4° C. as an undiluted solution sample.

(2) Undiluted Solution Sample Prepared Using Serum-Free Medium

HRC23 was cultured in Eagle's MEM with 10% FBS in the same manner as that of passage. The Eagle's MEM used was an antibiotic- and phenol red-free medium. HRC23 was cultured in a flask until cell growth reached a confluent state, and was further cultured to overgrowth (overpopulation). Then, the medium was replaced with serum-free Eagle's MEM not containing antibiotics and phenol red, followed by incubation at 37° C. under 5% $CO_2$ for 5 to 7 hours, during which the cells were rinsed several times with the same serum-free Eagle's MEM as above. The medium was finally replaced with the same serum-free Eagle's MEM as above, followed by incubation at 37° C. under 5% $CO_2$. After nine days, death of the cells was observed in morphological aspect of HRC23. After that, the medium was recovered and centrifuged at $3 \times 10^3 \times g$ for 10 minutes to obtain a supernatant. This supernatant was filtered with a 0.1 μm membrane filter (Millex® VV, Merck & Co., Inc. (Millipore)), and the filtrate was stored aseptically at 4° C. as an undiluted solution sample.

In addition, this undiluted solution sample was ultrafiltered to collect a fraction with a molecular weight of 1 kDa or less (Stirred Cell Model 8050 equipped with Ultracel® Amicon® YM1 and Ultracel® ultrafiltration membrane PLAC04310, Merck & Co., Inc. (Millipore)), and the resultant one was stored aseptically at 4° C.

(3) Undiluted Solution Sample Prepared Using Physiological Buffer Salt Solution

HRC23 was cultured in Eagle's MEM with 10% FBS in the same manner as that of passage. The Eagle's MEM used was an antibiotic- and phenol red-free medium. HRC23 was cultured in a flask until cell growth reached a confluent state, and was further cultured to overgrowth (overpopulation). Then, the medium was replaced with Hanks' balanced salt solution without antibiotics and glucose (pH 7.3, also referred to as HBSS−), followed by incubation at 37° C. under 5% $CO_2$ for 5 to 7 hours, during which the cells were rinsed several times with the same Hanks' balanced salt solution as above. After that, the cells were incubated at 37° C. under 5% $CO_2$ in the final Hanks' balanced salt solution which is the same as that described as above. After four days, death of the cells was observed in morphological aspect of HRC23. After that, the Hanks' balanced salt solution was recovered and centrifuged at $2 \times 10^3 \times g$ for 10 minutes to obtain a supernatant. This supernatant was filtered with a 0.1 μm membrane filter (Millex® VV, Merck & Co., Inc. (Millipore)), and the filtrate was stored aseptically at 4° C. as an undiluted solution sample.

In addition, this undiluted solution sample was ultrafiltered to collect a fraction with a molecular weight of 1 kDa or less (Stirred Cell Model 8050 equipped with Ultracel® Amicon® YM1 and Ultracel® ultrafiltration membrane PLAC04310, Merck & Co., Inc. (Millipore)), and the resultant one was stored aseptically at 4° C.

Moreover, instead of glucose-free Hanks' balanced salt solution (HBSS−), glucose-free Earle's balanced salt solution (Earle) and glucose-free phosphate buffered saline (PBS(+)) were used to prepare undiluted solution samples. Table 2 shows the compositions of the glucose-free Hanks' balanced salt solution, the Earle's balanced salt solution, and the phosphate buffered saline.

TABLE 2

|  | HBSS− [g/L] | Earle [g/L] | PBS(+) (DPBS) [g/L] |
|---|---|---|---|
| NaCl | 8.00 | 6.80 | 8.00 |
| KCl | 0.40 | 0.40 | 2.00 |
| $CaCl_2$ | 0.14 | 0.20 | 0.10 |
| $MgSO_4$ | 0.098 | 0.10 |  |
| $MgCl_2·12H_2O$ |  |  | 0.10 |
| $NaH_2PO_4$ |  | 0.125 |  |
| $Na_2HPO_4·12H_2O$ | 0.139 |  | 2.90 |
| $KH_2PO_4$ | 0.06 |  | 0.20 |
| Glucose | Not Contained | Not Contained | Not Contained |
| $NaHCO_3$ | 0.35 | 2.20 |  |
| Vapor Layer | air | 5% $CO_2$ | air |

Example 2: Test for Cytocidal Activity (1) Preparation of Serial Dilution Series of Test Samples To the undiluted solution sample (serum-containing medium) prepared in Example 1 (1) above, 10% FBS, an amino acid-blended solution and a vitamin-blended solution for Eagle's MEM (KOHJIN BIO; the amino acid-blended solution was a 50 times concentrated solution, and the vitamin-blended solution was a 100 times concentrated solution), and glucose were newly added in amounts prescribed for Eagle's MEM. The pH of the resultant solution was adjusted to 7.1 to 7.4 with 7.5% $NaHCO_3$, and then a prescribed amount of glutamine and 10% volume of FBS were added to the resultant solution to prepare a test sample. This is for the purpose of supplementing the nutrients consumed after the final replacement of medium with serum-containing medium. This test sample was subjected to 2-fold serial dilution with a control medium (Eagle's MEM with 10% FBS) to prepare a serial dilution series of test samples.

To the undiluted solution sample (serum-free medium) prepared in Example 1 (2) above, an amino acid and a vitamin were added as in the case of the undiluted solution sample of the serum-containing medium. The pH of the resultant solution was adjusted, and then glutamine, 10% FBS, and glucose were added to the resultant solution to prepare a test sample. This test sample was subjected to 2-fold serial dilution with a control medium (Eagle's MEM with 10% FBS) to prepare a serial dilution series of test samples. In addition, for the undiluted solution sample, which was subjected to ultrafiltration to collect a fraction with a molecular weight of 1 kDa or less, a serial dilution series of test samples was prepared in the same manner.

To the undiluted solution sample (Hanks' balanced salt solution) prepared in Example 1 (3) above, an amino acid and a vitamin were added as in the case of the sample undiluted solution of the serum-containing medium. The pH of the resultant solution was adjusted, and then glutamine, 10% FBS, and glucose were added to the resultant solution to prepare a test sample. This test sample was subjected to 2-fold serial dilution with a control solution (Eagle's MEM with 10% FBS) to prepare a serial dilution series of test samples. In addition, for the undiluted solution sample, which was subjected to ultrafiltration to collect a fraction with a molecular weight of 1 kDa or less, a serial dilution series of test samples was prepared in the same manner.

(2) Measurement of Cell Survival Rate by MTT Assay

HRC23 was diluted at a dilution rate for ordinary passage, dispensed into a 96-well microplate, and cultured in Eagle's MEM with 10% FBS at 37° C. under 5% $CO_2$. After 24 hours (Day 1), the medium was replaced with 170 μL of each serially diluted test sample, and moreover was incubated with replacement twice with each fresh test sample every other day (Day 3 and Day 5). On Day 6, the cell survival rate was measured by MTT assay (n=3).

The MTT assay was carried out as follows. MTT (Dojindo) was dissolved in Dulbecco's phosphate buffered saline (PBS−) without calcium and magnesium to a concentration of 5 mg/mL that is a 10-fold concentrated solution. This was aseptically filtered with a 0.1 μm membrane filter, dispensed, and stored at 4° C. After the cells were washed with 200 μL of medium (Eagle's MEM with 10% FBS), the above-described 5 mg/mL MTT solution is added to each medium in an amount of 1/10 volume of the medium to obtain a solution containing 0.5 mM MTT, and 150 μL thereof was added to each well of the 96-well microplate. After incubation for 30 to 40 minutes at 37° C., the solution in each well was aspirated off and washed with 200 μL of the medium. Then, 200 μL of dimethyl sulfoxide was added to each well. The absorbance at a wavelength of 570 nm was measured with a microplate reader (Model 550, Bio-Rad Laboratories). The cell survival rate was calculated by the following formula.

$$\text{Cell Survival Rate (\%)} = \frac{(A \text{ sample} - A \text{ blank})}{(A \text{ control} - A \text{ blank})} \times 100 \quad [\text{Formula 1}]$$

$A_{sample}$ denotes the absorbance measured as described above using each of the serially diluted test samples.

$A_{control}$ denotes the absorbance measured as described above but without using each of the serially diluted test samples.

$A_{blank}$ denotes the absorbance measured as described above but without HRC23.

Figure 2:
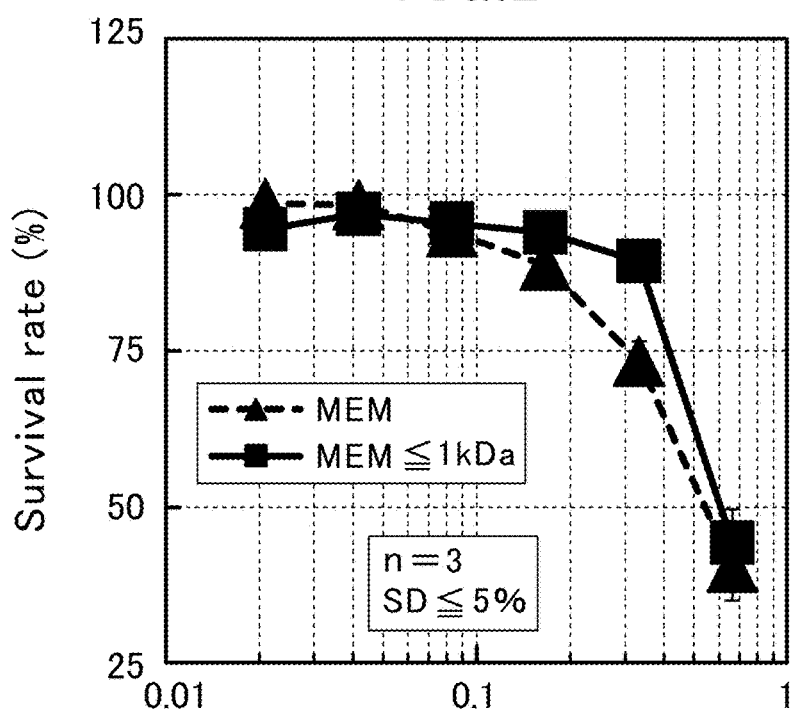
FIG. 2 is a semi-log graph illustrating the average value and standard deviation of HRC23 cell survival rate measured by MTT assay in a serial dilution series of test samples prepared from HRC23 using a serum-free medium (Eagle's MEM). "MEM≤1 kDa" is the fraction with a molecular weight of 1 kDa or less of the sample prepared using the Eagle's MEM. The horizontal axis represents the concentration of the test sample (undiluted solution mL/mL) on a common logarithmic scale.
Figure 3:
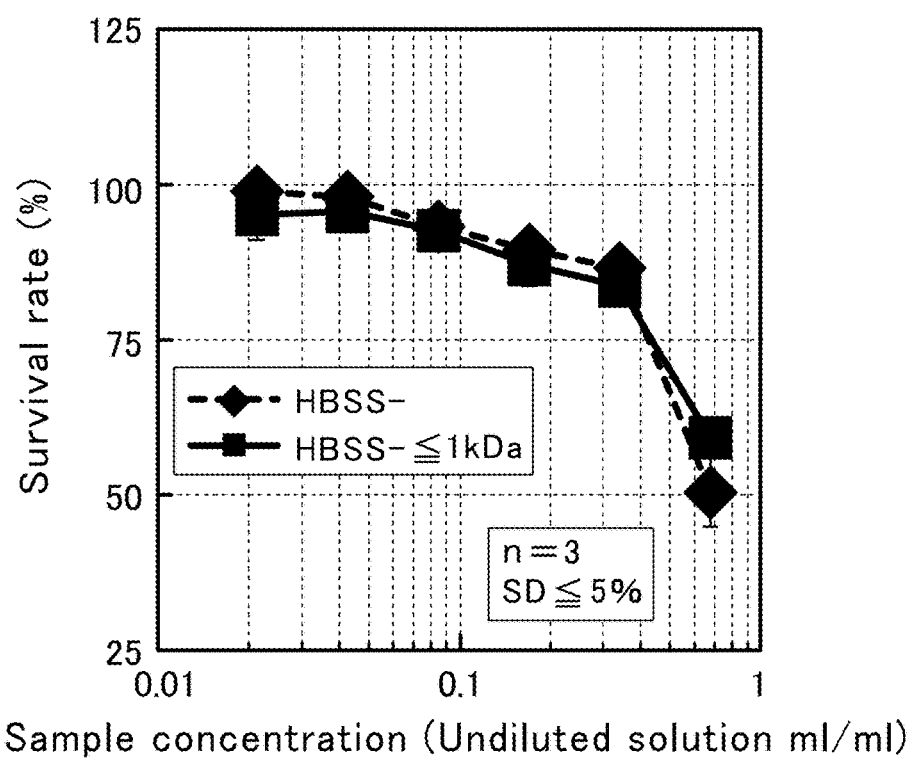
FIG. 3 is a semi-log graph illustrating the average value and standard deviation of HRC23 cell survival rate measured by MTT assay in a serial dilution series of test samples prepared from HRC23 using a physiological buffer salt solution (glucose-free Hanks' balanced salt solution: HBSS−). "HBSS−≤1 kDa" is the fraction with a molecular weight of 1 kDa or less of the sample prepared using the HBSS−. The horizontal axis represents the concentration of the test sample (undiluted solution mL/mL) on a common logarithmic scale.

FIGS. 1 to 3 present the results. A concentration-dependent cytocidal activity was observed in any of the sample prepared using the serum-containing medium, the sample prepared using the serum-free medium, and the sample prepared using the physiological buffered salt solution. In addition, a concentration-dependent cytocidal activity was similarly observed in the fraction with a molecular weight of 1 kDa or less of the sample prepared using the serum-free medium and the fraction with a molecular weight of 1 kDa or less of the sample prepared using the physiological buffer salt solution.

The sample prepared using physiological buffer salt solution is one prepared using glucose-free Hanks' balanced salt solution, that is, a medium without nutrients and energy sources. To put it differently, this indicates that the cells produced a substance having cytocidal activity, as in the case of the presence of nutrients and energy sources, even though the supply of external nutrients and energy sources was blocked. This is a surprising result. It has been revealed from the result that cells produce a substance having cytocidal activity using only the substances present in the cells as materials, and cause themselves to die.

Example 3: Preparation of Cell Extract Component Having Cytocidal Activity (1) Concentration For large scale culture, an undiluted solution sample was prepared using a flask with a surface area of 181 $cm^2$ in the same manner as the case of preparing the undiluted solution sample in Example 1 (3) above. Glucose-free Hanks' balanced salt solution (HBSS−) was used as a physiological buffer salt solution, and 40 mL of HBSS− was used in the final physiological buffer salt solution replacement. The undiluted solution sample thus obtained was evaporated to dryness under reduced pressure, and ethanol was added to a dried residue in an amount of 1/10 volume of the undiluted solution ample to dissolve the dried residue. Centrifugation was carried out at $3 \times 10^3 \times g$ for 10 minutes to obtain a supernatant, followed by evaporation to dryness under reduced pressure again. This ethanol extraction was repeated to obtain a dried product concentrated to about 1000 times of the undiluted solution sample. This dried product was stored at −80° C.

(2) Gel Filtration Chromatography

The dried product obtained in Example 3 (1) above was dissolved in pure water and washed with a liquid mixture of chloroform and ethyl acetate, from which the aqueous layer was recovered to obtain a sample. The washed sample was dissolved in 300 μL of 50 mM $Na_2SO_4$, and gel filtration chromatography was carried out with the following apparatus and conditions.

Figure 4:
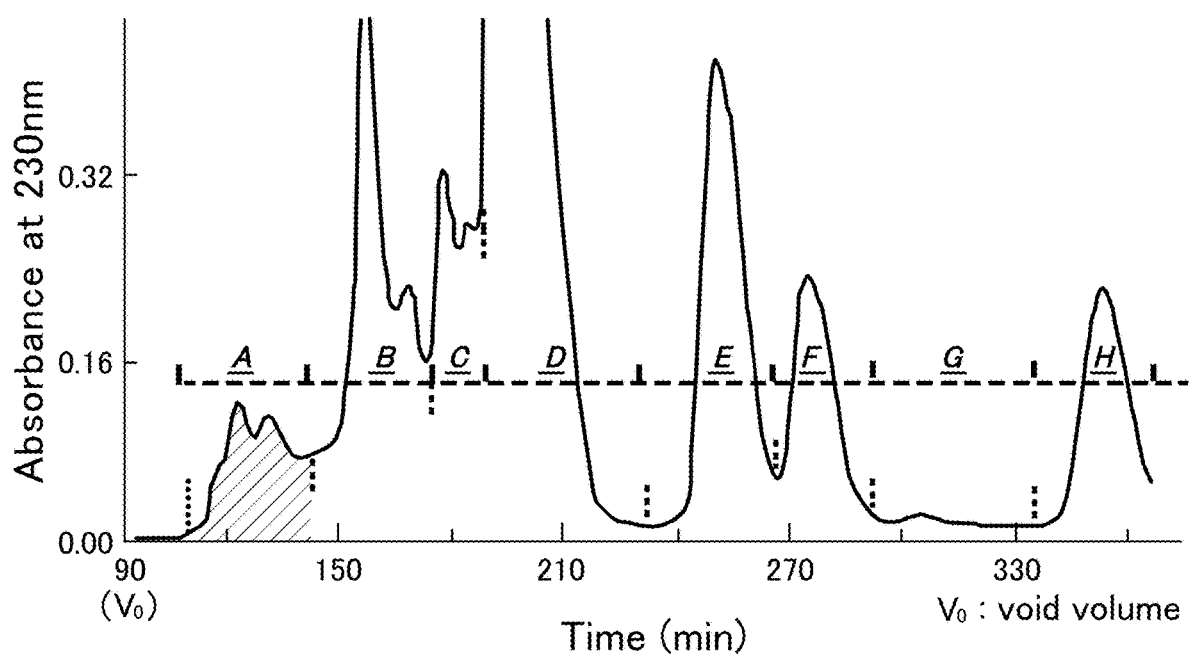
FIG. 4 is a chromatogram by gel filtration chromatography. Of the eight fractions A to H, the fraction A in which cytocidal activity was detected (105 to 141 minutes) is indicated with hatching.

Liquid feed pump: 880 PU (JASCO Corporation)
Detector: 825 UV (JASCO Corporation)
Mixer: HG-980-31 (JASCO Corporation)
Injector: Rheodyne 8125 (Rheodyne)
Column: Superformance (26 mm×600 mm) (Merck & Co., Inc.)
Carrier: HP Cellulofine sf (CHISSO CORPORATION)
Mobile phase: 50 mM $Na_2SO_4$
Flow rate: 0.6 ml/min
Fraction size: 1.8 ml (3 min)
Detection: 230 nm; Sensitivity: 0.16 aufs FIG. 4 presents the results of gel filtration chromatography. The eight fractions A to H illustrated in FIG. 4 were collected, and cytocidal activity was measured for each fraction by MTT assay. As a result, cytocidal activity was detected only in the fraction A (105 to 141 min).

The MTT assay here was carried out as follows. HRC23 was diluted at a dilution rate for ordinary passage, dispensed into a 96-well microplate, and cultured in Eagle's MEM with 10% FBS at 37° C. under 5% $CO_2$. After 24 hours, the medium was replaced with 170 μL of sample prepared from each fraction, followed by incubation for 2 days. Then, 200 μL of dimethyl sulfoxide was added to each well. The absorbance at a wavelength of 570 nm was measured with a microplate reader (Model 550, Bio-Rad Laboratories). The sample was prepared as follows. The aliquot of each fraction was added with the same volume of methanol, followed by filtration through a 0.22 μm membrane filter (Millex® GV, Merck & Co., Inc. (Millipore)) to remove $Na_2SO_4$. After that, a dried product obtained by drying the filtrate was dissolved in Eagle's MEM with 10% FBS and subjected to 2-fold serial dilution.

Figure 5:
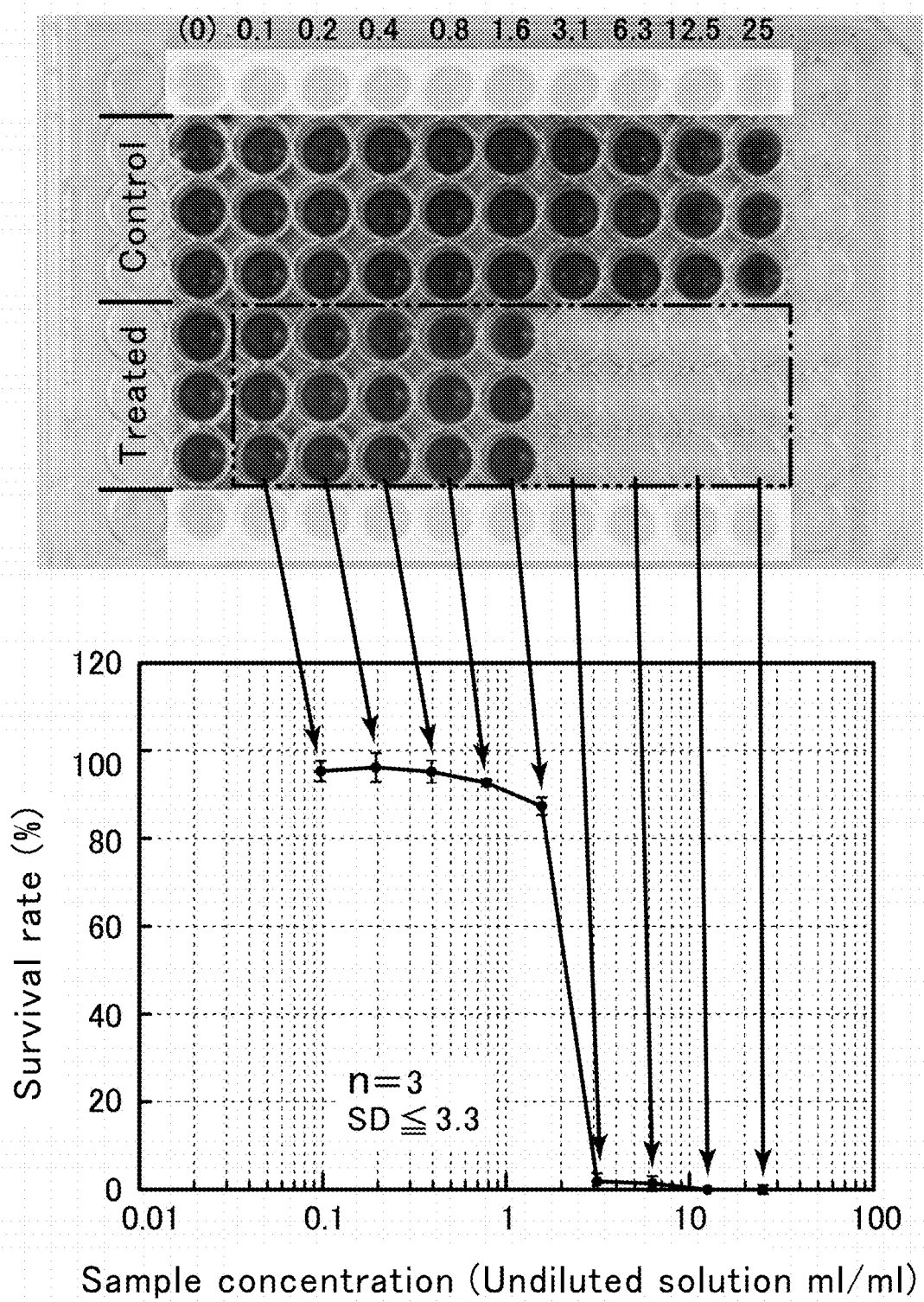
FIG. 5 illustrates the appearance of color development on a microplate observed by MTT assay in a serial dilution series for the fraction A obtained by gel filtration chromatography, together with a semi-log graph illustrating the average value and standard deviation of the measured cell survival rate. The horizontal axis represents the concentration of the test sample (undiluted solution mL/mL) on a common logarithmic scale.

FIG. 5 illustrates the appearance of color development on a microplate observed by MTT assay, together with a graph illustrating the concentration dependence of the cell survival rate. In FIG. 5, the sample concentration is in terms of undiluted solution.

The fraction A recovered was added with the same volume of methanol, followed by filtration through a 0.22 μm membrane filter (Millex® GV, Merck & Co., Inc. (Millipore)) to remove $Na_2SO_4$. After that, the filtrate was evaporated to dryness under reduced pressure, and the resultant dried product was stored at −80° C.

(3) Ion Exchange Chromatography

The dried product obtained in Example 3 (2) above was dissolved in 200 μL of 0.15 M $Na_2SO_4$, which was used as a sample to carry out ion exchange chromatography with the following apparatus and conditions. The active fractions were separated using the linear concentration gradient method of $Na_2SO_4$ on a strong cation exchange resin.
Liquid feed pump: 880 PU (JASCO Corporation)
Detector: 825 UV (JASCO Corporation)
Mixer: HG-980-31 (JASCO Corporation)
Injector: Rheodyne 8125 (Rheodyne)
Column: Resource™ S; 1 ml (GE Healthcare), two columns were used in series Elution was carried out by the linear concentration gradient method as shown in Table 3.
Flow rate: 0.25 ml/min
Fraction size: 0.75 ml (3 min)
Mobile phase: A; $H_2O$, B; 0.3M $Na_2SO_4$
Detection: 230 nm; Sensitivity: 0.16 aufs

TABLE 3

|  | Elution Program | | | |
| --- | --- | --- | --- | --- |
| Time (Min) | 0 | 30 | 150 | 151 |
| Mobile Phase A (%) | 50 | 50 | 20 | 1 |
| Mobile Phase B (%) | 50 | 50 | 80 | 99 |

The sample was injected into a column previously equilibrated with 0.15 M $Na_2SO_4$ solution, followed by washing with the solution for 30 minutes. After that, elution was carried out by the linear concentration gradient method of 0.15 M to 0.24 M $Na_2SO_4$.

Figure 6:
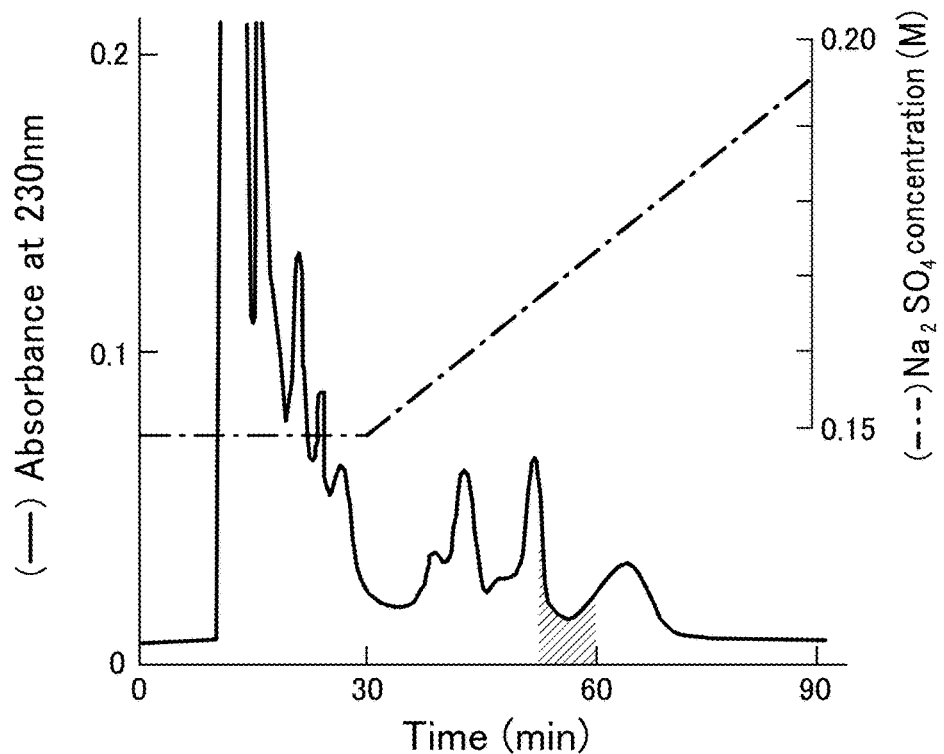
FIG. 6 is a chromatogram by ion exchange chromatography, and illustrates with hatching the fractions in which cytocidal activity was detected (fractions with $Na_2SO_4$ concentration of 165 to 170 mM).

FIG. 6 presents the results of ion exchange chromatography. Cytocidal activity was measured for each fraction by MTT assay, and cytocidal activity was detected only in fractions 18 to 21 having a $Na_2SO_4$ concentration of 165 to 170 mM. The MTT assay here was carried out in the same manner as in Example 3 (2) above.

Each of the recovered fractions having a $Na_2SO_4$ concentration of 165 to 170 mM was added with the same volume of methanol, followed by filtration through a 0.22 μm membrane filter (Millex® GV, Merck & Co., Inc. (Millipore)) to remove $Na_2SO_4$. After that, the filtrate was evaporated to dryness under reduced pressure, and the resultant dried product was stored at −80° C.

(4) Re-Gel Filtration Chromatography

Figure 7:
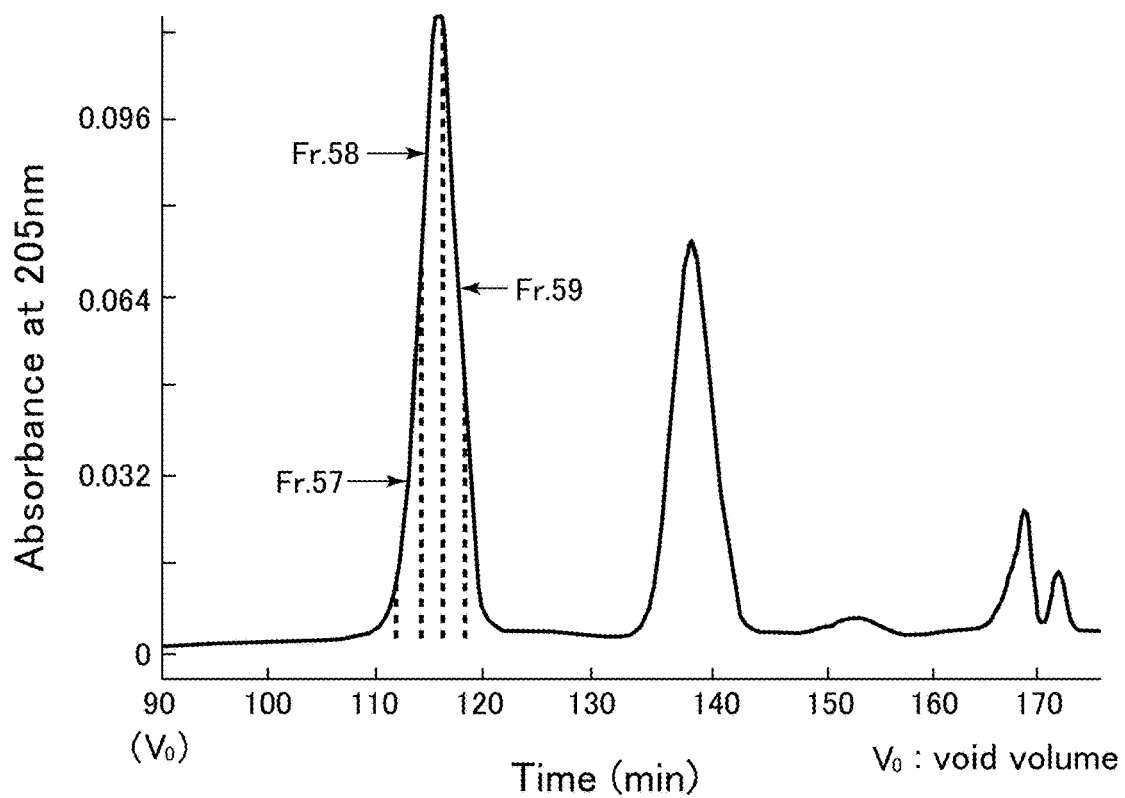
FIG. 7 is a chromatogram by gel filtration chromatography. The cytocidal activity is detected in the earlier peak, which includes three fractions (Fr57, Fr58, and Fr59).

The dried product obtained in Example 3 (3) above was dissolved in 300 μL of 50 mM $Na_2SO_4$, which was used as a sample to carry out gel filtration chromatography again with the following apparatus and conditions.
Liquid feed pump: 880 PU (JASCO Corporation)
Detector: 825 UV (JASCO Corporation)
Mixer: HG-980-31 (JASCO Corporation)
Injector: Rheodyne 8125 (Rheodyne)
Column: Superformance (26 mm×600 mm) (Merck & Co., Inc.)
Carrier: HP Cellulofine sf (CHISSO CORPORATION)
Mobile phase: 50 mM $Na_2SO_4$
Flow rate: 0.6 ml/min
Fraction size: 1.2 ml (2 min)
Detection: 205 nm; Sensitivity: 0.16 aufs FIG. 7 presents the results of gel filtration chromatography. Cytocidal activity was measured for each fraction by MTT assay, and cytocidal activity was observed in three fractions of fraction 57 (elution time 112 to 114 min), fraction 58 (elution time 114 to 116 min), and fraction 59 (elution time 116 to 118 min) in the earlier absorption peak. The cytocidal activity was strongly observed especially in fraction 58. The MTT assay here was carried out in the same manner as in Example 3 (2) above.

Each of the three recovered fractions was added with the same volume of methanol, followed by filtration through a 0.22 μm membrane filter (Millex® GV, Merck & Co., Inc. (Millipore)) to remove $Na_2SO_4$. After that, the filtrate was evaporated to dryness under reduced pressure to obtain a dried product.

(5) Mass Spectrometry (TOF-MS)

The dried product obtained in Example 3 (3) above was resuspended in 10 μL of a buffer solution composed of 5 mg/mL α-cyano-4-hydroxycinnamic acid (α-CHCA) in acetonitrile:water:TFA (50:50:1), which was used as a sample and analyzed by mass spectrometry with the following apparatus and conditions.

Analysis was carried out according to the peptide analysis program using the following.
Analytical instrument: Voyager System 6366 (Applied Biosystem)
Applied voltage: +20000 V
Sample introduction: manual; MALDI plate
Matrix: α-Cyano-4-hydroxycinnamic acid (α-CHCA) (Tokyo Chemical Industry Co., Ltd.)

Figure 8:
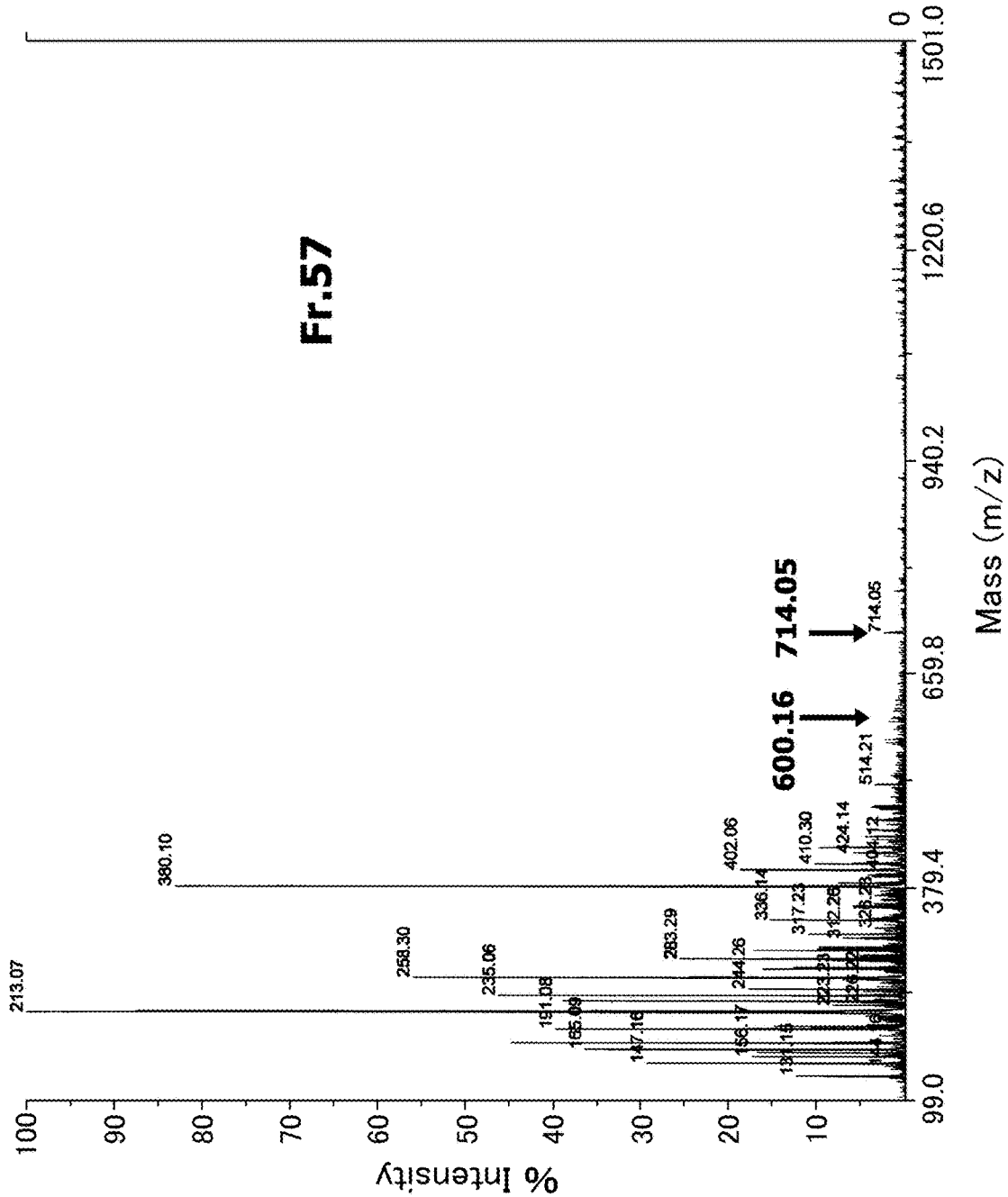
FIG. 8 is a mass spectrum for fraction 57.
Figure 9:
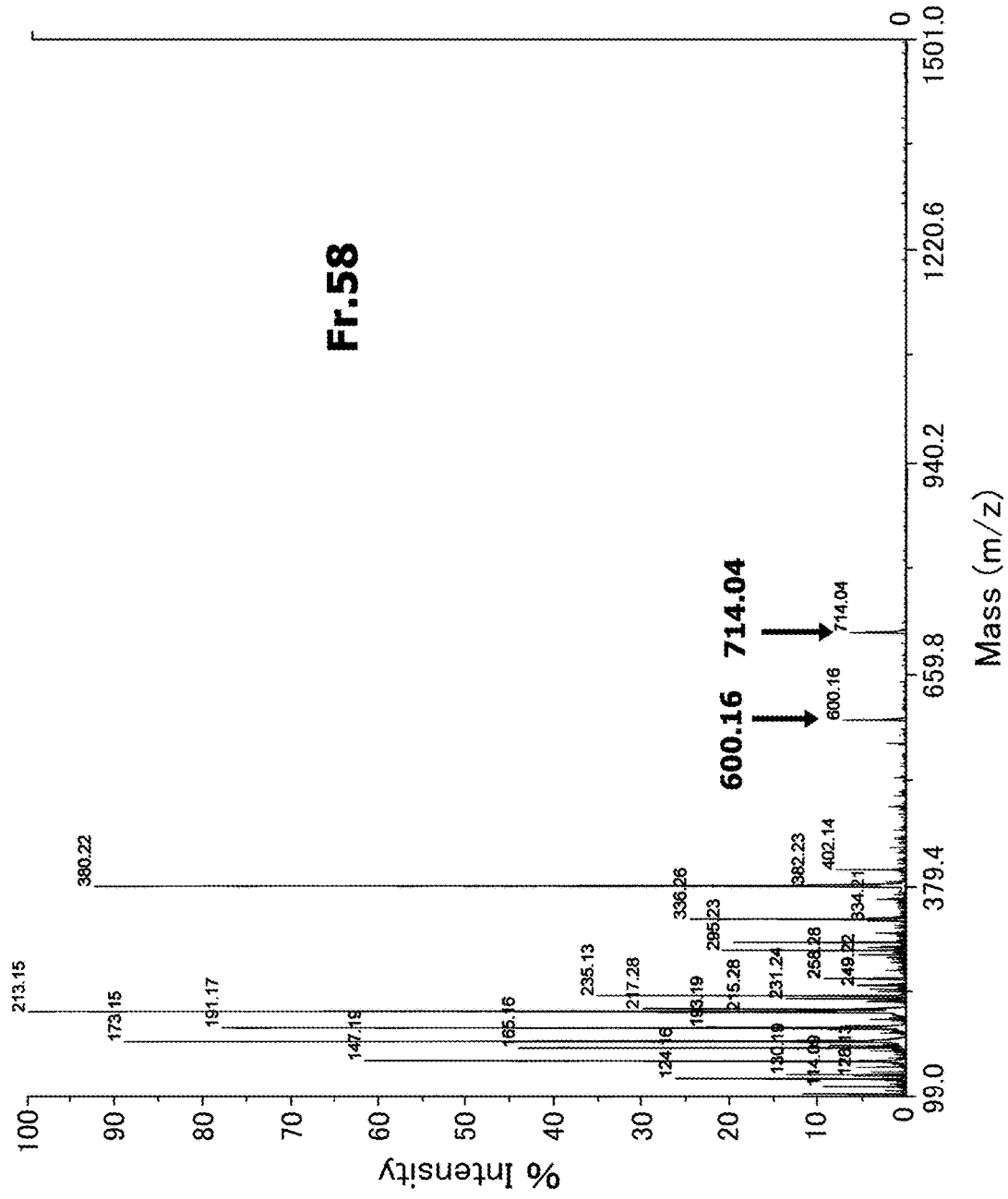
FIG. 9 is a mass spectrum for fraction 58.
Figure 10:
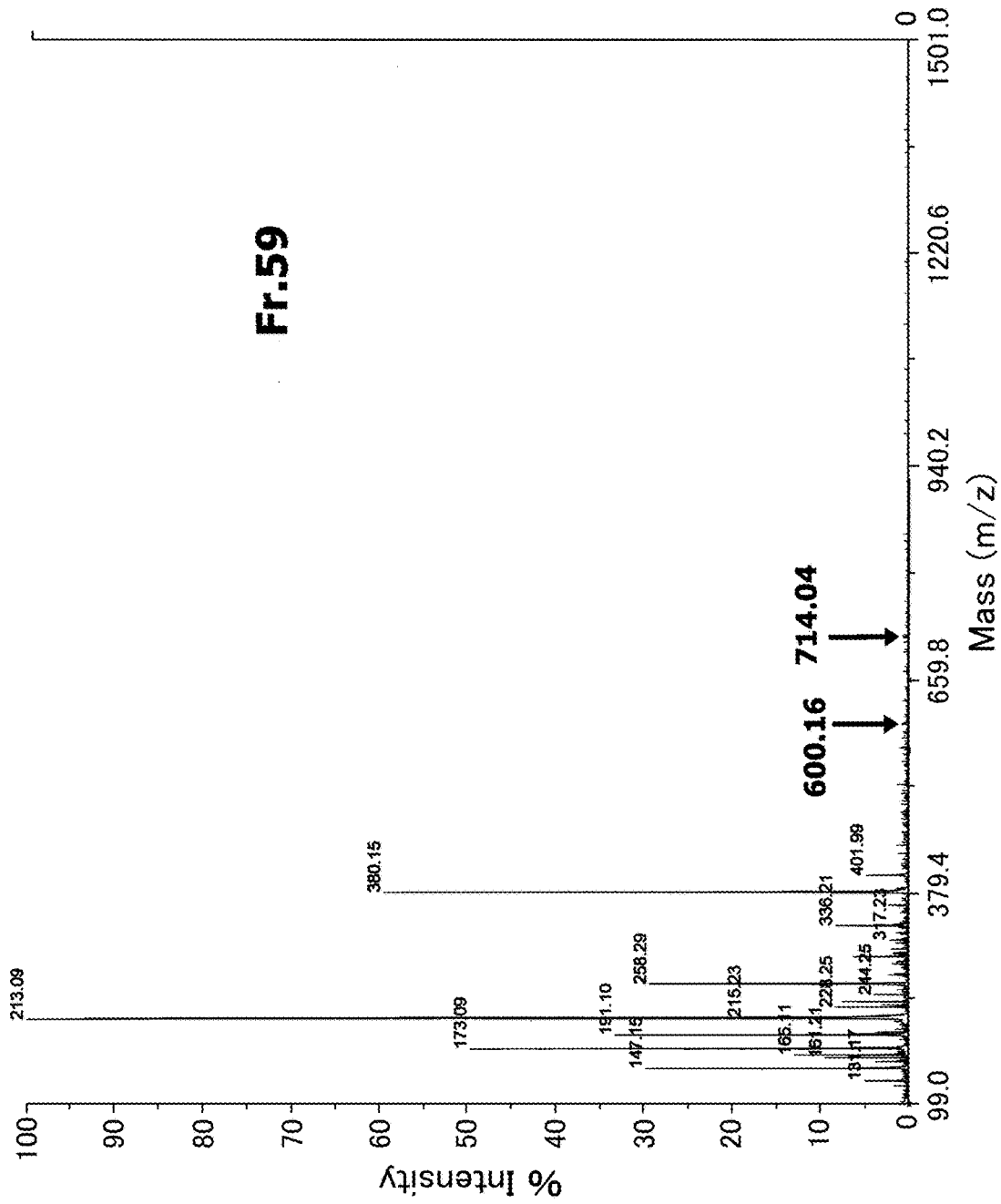
FIG. 10 is a mass spectrum for fraction 59.
Figure 11:
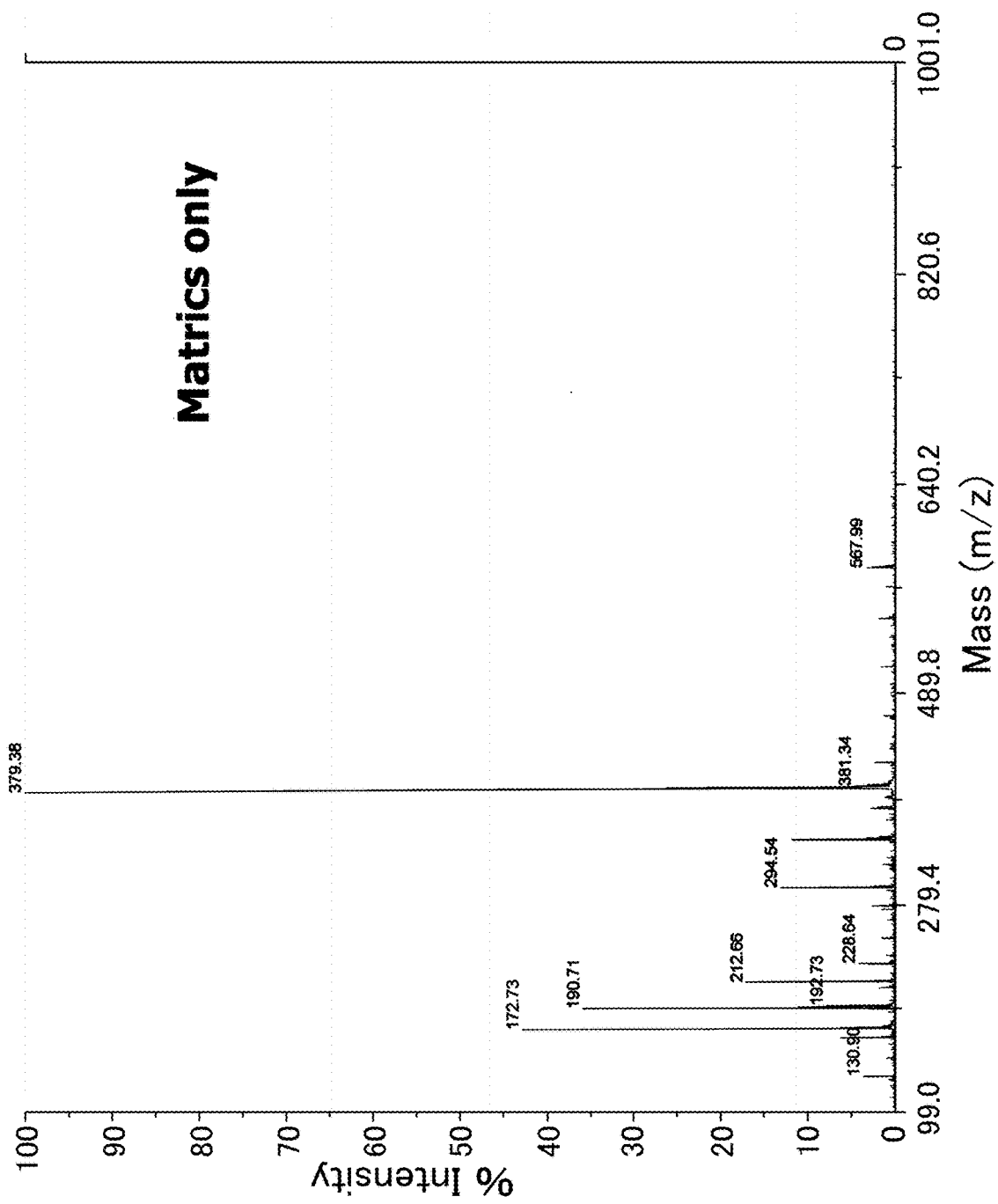
FIG. 11 is a mass spectrum for matrix only.

FIGS. 8 to 10 present the results obtained from the three fractions (57, 58, and 59) with m/z values of 100 to 1500. In addition, FIG. 11 presents the results obtained from the matrix alone with m/z values of 100 to 1000.

Figure 12:
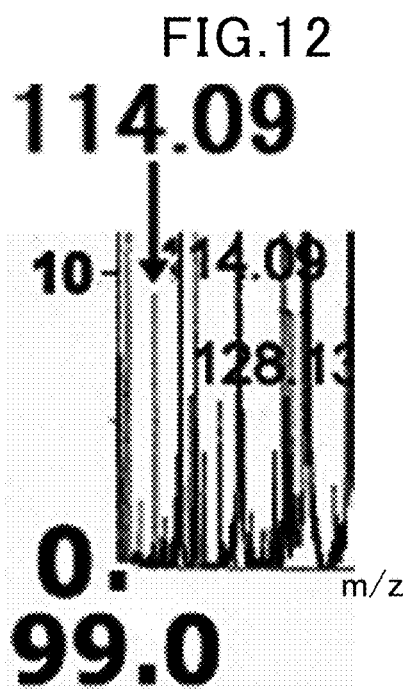
FIG. 12 is an enlarged diagram of the vicinity of signals at the m/z value of 114.09 in the spectrum of fraction 58.

In each of the mass spectra for the three fractions (57, 58, and 59), signals were observed at m/z values of 600 and 714. In particular, strong signals were observed at m/z values of 600.16 and 714.04 in the spectrum of fraction 58, while the signals were not as clear in the spectrum of fraction 59 as in fractions 57 and 58. In addition, in the spectrum of fraction 58, a signal was clearly observed at m/z value of 114.09 (an enlarged diagram is illustrated as FIG. 12).

Meanwhile, no signal having an m/z value greater than the m/z value of 1000 was observed. Therefore, it is suggested that the cell extract component having cytocidal activity has a molecular weight of 1 kD or less. This is consistent with the results of FIGS. 2 and 3 indicating that cytocidal activity was observed in a fraction having a molecular weight of 1 kDa or less.

However, in light of the fact that there are many signals having m/z values of 300 or less also in the mass spectra obtained as described above, the identification of a cell extract component having cytocidal activity is considered to require further detailed examination including examination on the stability of the component.

Example 4: Measurement of Cytocidal Activity Against Various Cancer Cells

The dried product obtained in Example 3 (2) above was subjected to 2-fold serial dilution using the culture media used for culturing HRC23, MKN74, LK2, VMRC-JCP, SKN, and LLC to prepare a serial dilution series of test samples. Each of HRC23, MKN74, LK2, VMRC-JCP, SKN, and LLC was separately seeded in a 96-well microplate in an amount for establishing an approximately 80% confluent state in 3 days of culture, and was cultured for 24 hours at 37° C. under 5% $CO_2$ in the predetermined culture medium. The medium was replaced with 170 µL of test sample, followed by incubation for 2 days. Then, 200 µL of dimethyl sulfoxide was added to each well. The absorbance at a wavelength of 570 nm was measured with a microplate reader (Model 550, Bio-Rad Laboratories) and MTT assay was carried out (n=3).

Figure 13:
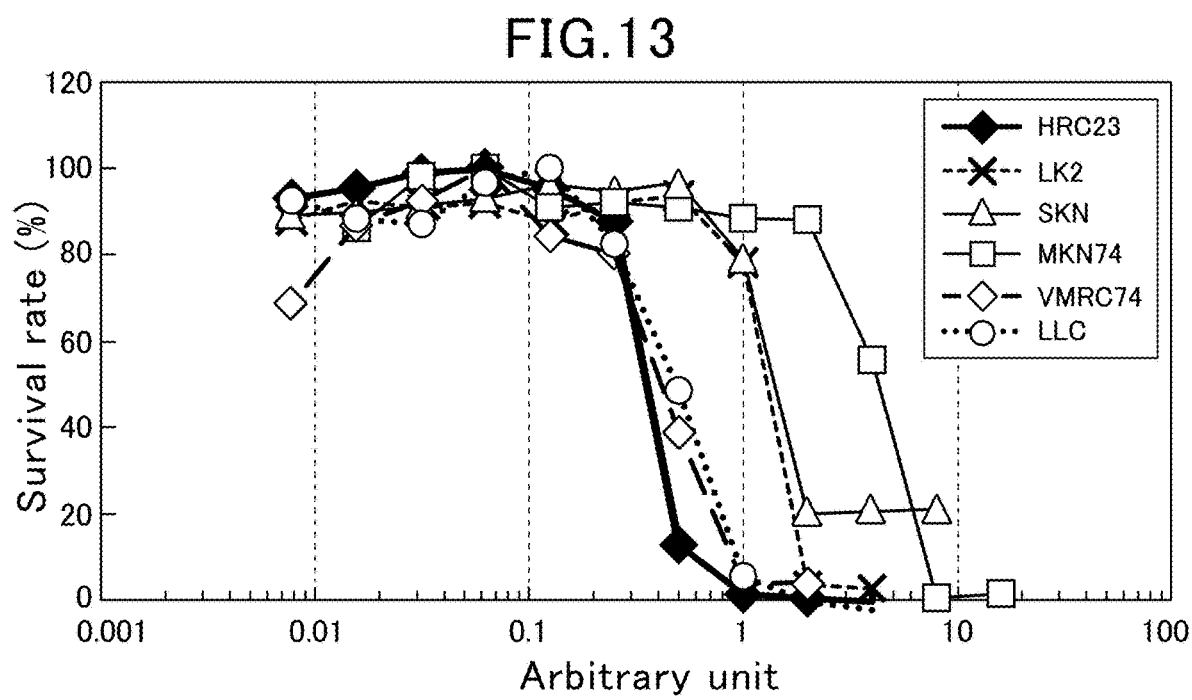
FIG. 13 is a semi-log graph illustrating the average value and standard deviation of cell survival rate of various cells measured by MTT assay in a serial dilution series of test samples prepared from HRC23 using a physiological buffer salt solution (glucose-free Hanks' balanced salt solution: HBSS−). The horizontal axis is represented on a common logarithmic scale, where the minimum concentration of the test sample exhibiting 0% survival rate for HRC23 is expressed as 1 in arbitrary unit.

FIG. 13 illustrates a graph of cell survival rate of various cancer cells measured by MTT assay. The horizontal axis is represented on a common logarithmic scale, where the minimum concentration of the test sample exhibiting 0% survival rate for HRC23 is expressed as 1 in arbitrary unit. The results have revealed that the test sample having cytocidal activity obtained from HRC23 is also effective against cancers other than HRC23, and commonly exhibits cytocidal activity in a concentration-dependent manner regardless of the type of cancer and tissue type.

Example 5: Measurement of Cytocidal Activity in LLC- or SKN-Derived Sample (1) Preparation of Undiluted Solution Sample LLC and SKN were cultured in Eagle's MEM with 10% FBS in the same manner as that of HRC23. The Eagle's MEM used was an antibiotic- and phenol red-free medium. LLC and SKN were cultured in a flask until their cell growth reached a confluent state, and were further cultured for one day. After washing with Hanks' balanced salt solution without antibiotics and glucose, incubation was carried out at 37° C. under 5% $CO_2$ in 5 mL Hanks' balanced salt solution/flask. After death of LLC and SKN had been observed in morphological aspect of the cells, Hanks' balanced salt solution was recovered and centrifuged at 1,500×g for 10 minutes to obtain supernatants. These supernatants were filtered with a 0.1 µm membrane filter (Millex® VV, Merck & Co., Inc. (Millipore)), and the filtrates were each used as an undiluted solution sample.

In addition, each of these undiluted solution samples was ultrafiltered to collect a fraction with a molecular weight of 1 kDa or less (Stirred Cell Model 8050 equipped with Ultracel® Amicon® YM1 and Ultracel® ultrafiltration membrane PLAC04310, Merck & Co., Inc. (Millipore)).

(2) Measurement of Cell Survival Rate by MTT Assay

To the undiluted solution sample prepared in Example 5 (1) above, 10% FBS, amino acid- and vitamin-blended solutions for Eagle's MEM, and glucose were added in amounts prescribed for Eagle's MEM. The pH of the resultant solution was adjusted with 7.5% $NaHCO_3$ to prepare a test sample. This test sample was subjected to 2-fold serial dilution with a control solution (Hanks' balanced salt solution with 50-fold concentration amino acid-blended solution and a 100-fold concentration vitamin-blended solution for Eagle's MEM) to prepare a serial dilution series of test samples. In addition, the undiluted solution sample was subjected to ultrafiltration to collect a fraction with a molecular weight of 1 kDa or less, for which a serial dilution series was prepared in the same manner.

Figure 14:
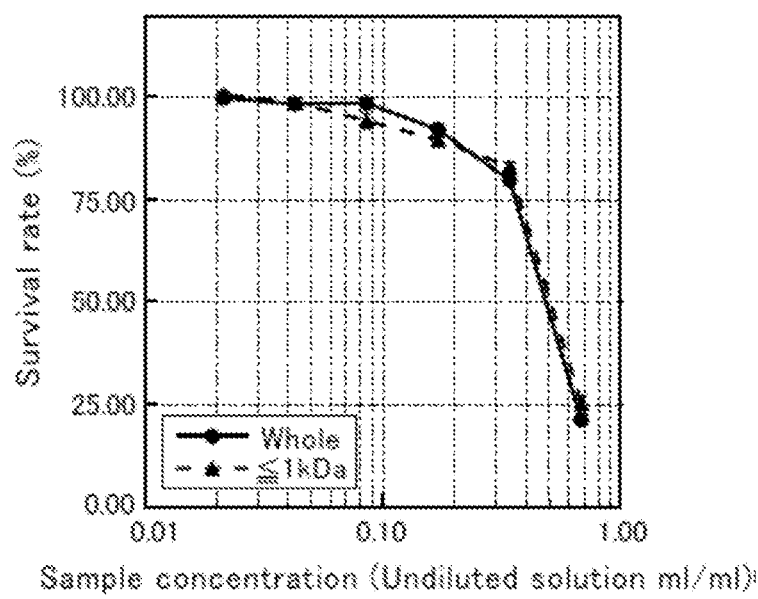
FIG. 14 is a semi-log graph illustrating the average value and standard deviation of HRC23 cell survival rate measured by MTT assay in a serial dilution series of test samples prepared from LLC using a physiological buffer salt solution (glucose-free Hanks' balanced salt solution: HBSS−). "Whole" refers to the whole sample and "≤1 kDa" refers to the fraction of the sample with a molecular weight of 1 kDa or less. The horizontal axis represents the concentration of the test sample (undiluted solution mL/mL) on a common logarithmic scale.
Figure 15:
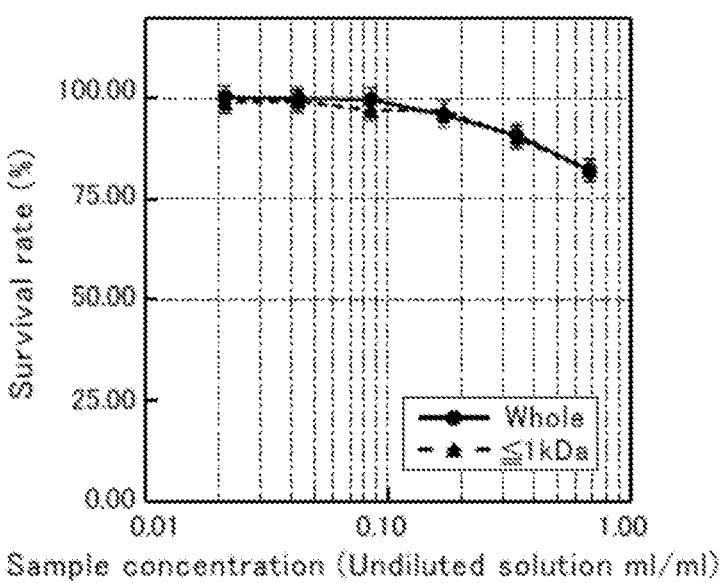
FIG. 15 is a semi-log graph illustrating the average value and standard deviation of HRC23 cell survival rate measured by MTT assay in a serial dilution series of test samples prepared from SKN using a physiological buffer salt solution (glucose-free Hanks' balanced salt solution: HBSS−). "Whole" refers to the whole sample and "≤1 kDa" refers to the fraction of the sample with a molecular weight of 1 kDa or less. The horizontal axis represents the concentration of the test sample (undiluted solution mL/mL) on a common logarithmic scale.

MTT assay was carried out according to the method described in Example 2 (2) above to measure the HRC23 cell survival rate (n=3). FIGS. 14 and 15 present the results.

Both the LLC-derived sample and the SKN-derived sample also exhibited cytocidal activity against HRC23 in the same manner as the HRC23-derived sample. The result that the LLC-derived sample exhibited cytocidal activity against HRC23 and the result in Example 4 (the HRC23-derived sample exhibited cytocidal activity against LLC) mean that cross reactions across species were observed. In addition, SKN is a rare non-epithelial malignant tumor cell, and it has been confirmed that non-epithelial malignant tumor cells such as SKN also produce a substance having cytocidal activity. As for the SKN-derived sample, the cytocidal activity observed was weaker than that of the LLC-derived sample and the HRC23-derived sample. This seems to be because the number of SKN cells after culturing was much smaller than that of LLC or HRC23.

Example 6: Measurement of Cytocidal Activity when Using Various Physiological Buffer Salt Solutions To the undiluted solution samples prepared in Example 1 (3) above (HBSS−, Earle, and PBS(+)), 10% FBS, 50-fold concentration amino acid- and 100-fold concentration vitamin-blended solutions for Eagle's MEM, and glucose were added in amounts prescribed for Eagle's MEM. The pH of each resultant solution was adjusted with 7.5% $NaHCO_3$ to prepare test samples. Each of these test samples was subjected to 2-fold serial dilution with a control solution (HBSS−, Earle, or PBS(+) with 50-fold concentration amino acid-blended solution and a 100-fold concentration vitamin-blended solution for Eagle's MEM) to prepare a serial dilution series of test samples.

Figure 16:
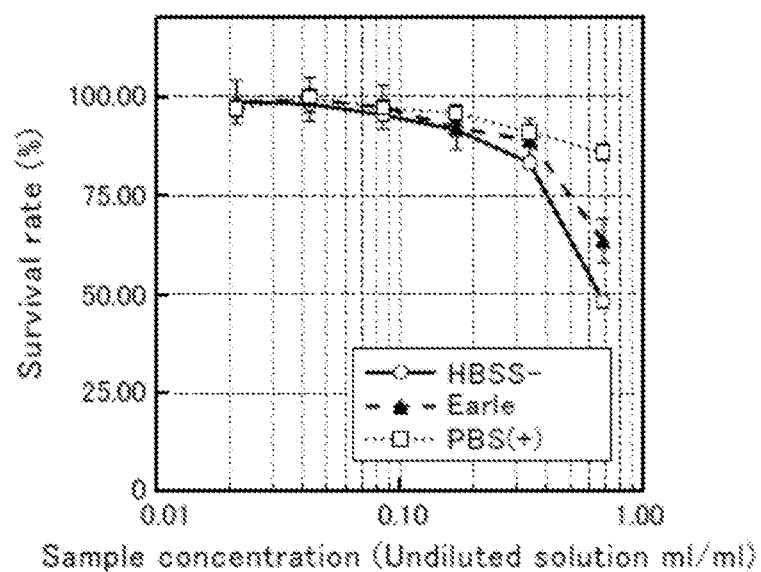
FIG. 16 is a semi-log graph illustrating the average value and standard deviation of HRC23 cell survival rate measured by MTT assay in a serial dilution series of test samples prepared from HRC23 using a physiological buffer salt solution (glucose-free Hanks' balanced salt solution: HBSS−, Earle's balanced salt solution: Earle, and phosphate buffered saline: PBS(+)). The horizontal axis represents the concentration of the test sample (undiluted solution mL/mL) on a common logarithmic scale.

MTT assay was carried out according to the method described in Example 2 (2) above to measure the HRC23 cell survival rate (n=3). FIG. 16 presents the results.

Cytocidal activity was observed with different intensities in each of the case using HBSS−, the case using Earle, and the case using PBS(+).

Example 7: Evaluation of Influence of Cell Culture States on Cytocidal Activity In the case of using an ordinary culture medium, since cells in the growth phase continue to grow, tests with different cell densities in the culture medium are difficult. However, use of Hanks' balanced salt solution containing no nutrient sources (glucose free) has made it possible to investigate the production of a component having cytocidal activity at the stage of growth phase.

HRC23 was seeded in 25 $cm^2$ passage culture flasks with different numbers of cells, and they were cultured in Eagle's MEM with 10% FBS. The Eagle's MEM used was an antibiotic- and phenol red-free medium. The cells were cultured in the flask with a large number of cells seeded until the cell growth reached a confluent state, and further cultured for one day. At this point in time, the cells in the flask with a small number of cells seeded was in the growth phase and the cell density was approximately 72% compared to the confluent state although the cell density was a level that does not pose an obstacle for passage. At this point in time, in any of the case of a large number of cells seeded and the case of a small number of cells seeded, the cells were washed with Hanks' balanced salt solution without antibiotics and glucose and then incubated at 37° C. under 5% $CO_2$ in 5 mL Hanks' balanced salt solution/flask. After death of the cells was observed in morphological aspect of HRC23, the Hanks' balanced salt solution was recovered and centrifuged at 1,500×g for 10 minutes to obtain a supernatant. This supernatant was filtered with a 0.1 μm membrane filter (Millex® VV, Merck & Co., Inc. (Millipore)), and the filtrate was used as an undiluted solution sample.

Figure 17:
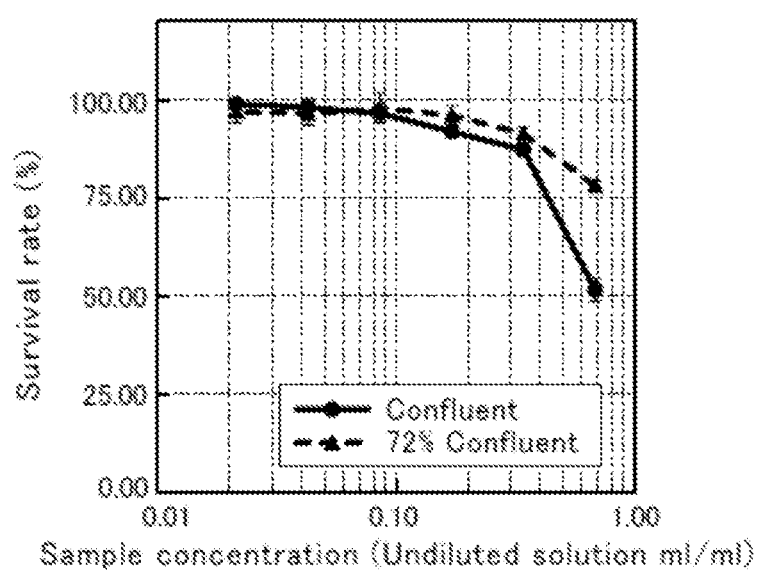
FIG. 17 is a semi-log graph illustrating the average value and standard deviation of HRC23 cell survival rate measured by MTT assay in a serial dilution series of test samples prepared from HRC23 with different cell densities after culturing using a physiological buffer salt solution (glucose-free Hanks' balanced salt solution: HBSS−). The horizontal axis represents the concentration of the test sample (undiluted solution mL/mL) on a common logarithmic scale.

MTT assay was carried out (in a 25 cm² passage culture flask) according to the method described in Example 2 (2) above to measure the HRC23 cell survival rate (n=3). FIG. 17 presents the results.

Cytocidal activity was observed with different intensities in each of the case of a large number of cells seeded and the case of a small number of cells seeded. Therefore, it has been revealed that even cells in the growth phase produce a component having cytocidal activity. This indicates that cells can intentionally produce a component having a cytocidal effect regardless of the phase of the cells.

Example 8: Measurement of Cytocidal Activity of LK-2-Derived Sample Against LK-2 and HRC23

(1) Preparation of Undiluted Solution Sample

LK-2 was cultured in RPMI 1640 with 10% FBS (Merck & Co., Inc. (Sigma-Aldrich Japan), R883) in the same manner as that of passage. LK-2 was cultured in a flask until cell growth reached a fully confluent state, and then the medium was finally replaced with 5 mL of RPMI 1640 with 10% FBS. In addition, apart from the above-described example of replacing the medium with RPMI 1640 with 10% FBS, LK-2 was cultured in a flask until cell growth reached a fully confluent state, and the cells were washed 4 times with 30 mL of Hanks' balanced salt solution without antibiotics and glucose, and then 5 mL of the Hanks' balanced salt solution was placed in a flask to immerse the cells.

The above two types of culture solutions were incubated at 37° C. under 5% $CO_2$, and the cells were cultured until death of the cells had been observed in morphological aspect of LK-2. After that, the medium and Hanks' balanced salt solution were recovered and centrifuged at 1,500×g for 10 minutes to obtain supernatants. These supernatants were filtered with a 0.1 μm membrane filter (Millex® VV, Merck & Co., Inc. (Millipore)), and the filtrates were each used as an undiluted solution sample. In addition, the undiluted solution sample obtained by using Hanks' balanced salt solution was ultrafiltered to collect a fraction with a molecular weight of 1 kDa or less (Stirred Cell Model 8050 equipped with Ultracel® Amicon® YM1 and Ultracel® ultrafiltration membrane PLAC04310, Merck & Co., Inc. (Millipore)).

(2) Preparation of Serial Dilution Series of Test Samples

To each of the undiluted solution samples prepared in Example 8 (1) above, an amino acid-blended solution (50-fold concentrated) (Merck & Co., Inc. (Sigma-Aldrich Japan), M5550) and a vitamin-blended solution (100-fold concentrated) (Merck & Co., Inc. (Sigma-Aldrich Japan), R7256) for RPMI 1640 were added. The pH of each resultant solution was adjusted to 7.2 to 7.3 with acetic acid, and then 10% FBS, 10% glucose, and 0.1 volume of 200 mM glutamine were added to each resultant solution to prepare test samples. Each test sample was subjected to 2-fold serial dilution in a control medium (RPMI 1640 with 10% FBS) to prepare a serial dilution series A of test samples. In addition, the undiluted solution sample was subjected to ultrafiltration to collect a fraction with a molecular weight of 1 kDa or less, for which a serial dilution series A (<1 kDa) was prepared in the same manner.

In addition, to each of the undiluted solution samples prepared in Example 8 (1) above, an amino acid-blended solution (50-fold concentrated) (same as above) and a vitamin-blended solution (100-fold concentrated) (same as above) for Eagle's MEM were added. The pH of each resultant solution was adjusted to 7.2 to 7.3 with acetic acid, and then 10% FBS, 10% glucose, and 0.1 volume of 200 mM glutamine were added to each resultant solution to prepare test samples. Each test sample was subjected to 2-fold serial dilution in a control medium (Eagle's MEM with 10% FBS) to prepare a serial dilution series B of test samples. In addition, the undiluted solution sample was subjected to ultrafiltration to collect a fraction with a molecular weight of 1 kDa or less, for which a serial dilution series B (<1 kDa) was prepared in the same manner.

(3) Measurement of Cell Survival Rate by MTT Assay

LK-2 was diluted at a dilution rate for ordinary passage, dispensed into a 96-well microplate, and cultured in RPMI 1640 with 10% FBS at 37° C. under 5% $CO_2$ for 24 hours. Then, each medium was replaced with 170 μL of a diluted solution of the serial dilution series A. After culturing for 24 hours in the diluted solutions of the serial dilution series A, each diluted solution was replaced with a fresh diluted solution of the serial dilution series A at the same dilution factor, and the culturing was carried out for another 24 hours. Also in the case of using the serial dilution series A (<1 kDa), LK-2 was cultured as in the case of using the serial dilution series A.

Figure 18:
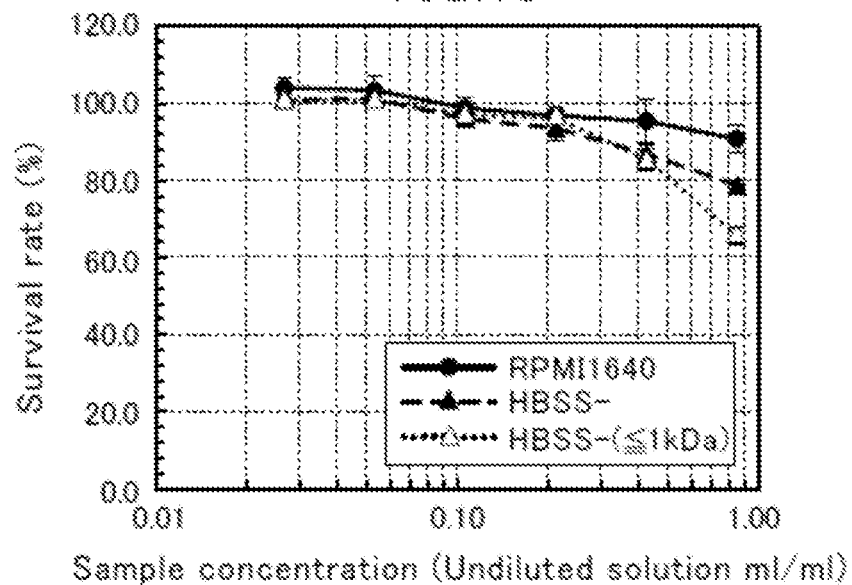
FIG. 18 is a semi-log graph illustrating the average value and standard deviation of LK-2 cell survival rate measured by MTT assay in a serial dilution series of test samples prepared from LK-2 using a serum-containing medium (RPMI 1640 with 10% FBS) or a physiological buffer salt solution (glucose-free Hanks' balanced salt solution: HBSS−). "HBSS−(≤1 kDa)" is the fraction of the sample with a molecular weight of 1 kDa or less prepared using the glucose-free Hanks' balanced salt solution (HBSS−). The horizontal axis represents the concentration of the test sample (undiluted solution mL/mL) on a common logarithmic scale.

MTT assay was carried out according to the method described in Example 2 (2) above to measure the LK-2 cell survival rate (n=3). FIG. 18 presents the results.

In addition, HRC23 was diluted at a dilution rate for ordinary passage, dispensed into a 96-well microplate, and cultured in Eagle's MEM with 10% FBS at 37° C. under 5% $CO_2$ for 24 hours. Then, each medium was replaced with 170 μL of a diluted solution of the serial dilution series B. After culturing for 24 hours in the diluted solutions of the serial dilution series B, each diluted solution was replaced with a fresh diluted solution of the serial dilution series B at the same dilution factor, and the culturing was carried out for another 24 hours. Also in the case of using the serial dilution series B (<1 kDa), HRC23 was cultured as in the case of using the serial dilution series B.

Figure 19:
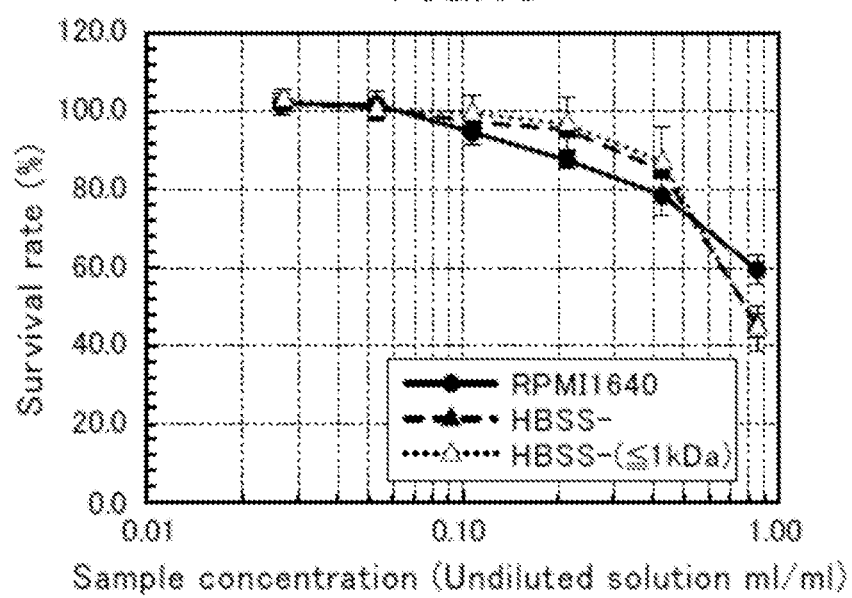
FIG. 19 is a semi-log graph illustrating the average value and standard deviation of HRC23 cell survival rate measured by MTT assay in a serial dilution series of test samples prepared from LK-2 using a serum-containing medium (RPMI 1640 with 10% FBS) or a physiological buffer salt solution (glucose-free Hanks' balanced salt solution: HBSS−). "HBSS− (≤1 kDa)" is the fraction of the sample with a molecular weight of 1 kDa or less prepared using the glucose-free Hanks' balanced salt solution (HBSS−). The horizontal axis represents the concentration of the test sample (undiluted solution mL/mL) on a common logarithmic scale.

MTT assay was carried out according to the method described in Example 2 (2) above to measure the HRC23 cell survival rate (n=3). FIG. 19 presents the results.

The LK-2-derived sample exhibited cytocidal activity against LK-2 and HRC23. In addition, the sample based on the undiluted solution sample obtained using Hanks' balanced salt solution exhibited stronger cytocidal activity than the sample based on the undiluted solution sample obtained by finally replacing the medium with RPMI 1640. This suggests that obtaining a component having cytocidal activity extracted from malignant tumor-derived cells using a physiological buffer salt solution such as Hanks' balanced salt solution may make it possible to achieve higher yields than using a culture medium to obtain the component, or may make it possible to obtain the target component without reducing cytocidal activity of the component.

Example 9: In Vivo Cytocidal Activity on Mice

Four mice (C57BL/6NCrSlc, male, 5 weeks of age) were inoculated intraperitoneally with 300 μL of LLC suspension ($2\times10^6$ cells) for LLC transplantation. After 1 week, the dried product obtained in the above [4] (2) equivalent to 1 L of undiluted solution was dissolved in 300 µL of FBS-free Eagle's MEM, and the resultant solution was intraperitoneally administered to two mice as a treatment group once a day for 6 days. The two mice in the control group, not subjected to the above treatment, died 25 days after LLC transplantation. On the other hand, in the treatment group, one died on day 35 and the other died on day 48 after LLC transplantation. A clear survival benefit was observed in the treatment group as compared with the control group. In the treatment group, no symptom that appeared to be a side effect was observed.

What is claimed is:

1. A method for producing a physiological buffer salt solution comprising a cytocidal component produced by malignant tumor cells, the method comprising:

culturing malignant tumor cells obtained from a malignant tumor or from an established malignant tumor cell line in a culture medium to a 60% to 100% confluent state;

replacing, after the culturing, the culture medium with a physiological buffer salt solution; and recovering the physiological buffer salt solution after the time at which death of the malignant tumor cells is observed in the physiological buffer salt solution in morphological aspect of said cells, wherein the recovered physiological buffer salt solution comprises a cytocidal component produced by the malignant tumor cells, wherein the physiological buffer salt solution is glucose-free.

2. The production method according to claim 1, wherein the physiological buffer salt solution is selected from the group consisting of Hanks' balanced salt solution, Earle's balanced salt solution, and phosphate buffered saline.

3. A method for preparing a cell extract cytocidal component isolated from or purified from malignant tumor cells, the method comprising:

culturing malignant tumor cells obtained from a malignant tumor or from an established malignant tumor cell line in a culture medium to a 60% to 100% confluent state;

replacing, after the culturing, the culture medium with a physiological buffer salt solution;

recovering the physiological buffer salt solution after the time at which death of the malignant tumor cells is observed in the physiological buffer salt solution in morphological aspect of said cells;

drying the recovered physiological buffer salt solution to obtain a dried product of the recovered physiological buffer salt solution, wherein the dried product contains a fraction with a molecular weight of 1 kDa or less in the recovered physiological buffer salt solution;

extracting the dried product using a solvent containing an alcohol having 1 to 3 carbon atoms, and drying a resultant solution;

dissolving a dried product of the resultant solution in water to obtain an aqueous solution, adding a non-polar organic solvent to the aqueous solution to form an aqueous layer and an organic layer, and extracting the aqueous layer; and separating a cell extract cytocidal component by chromatography of the extracted aqueous layer, wherein the physiological buffer salt solution is glucose-free.

4. The preparation method according to claim 3, wherein the chromatography includes gel filtration chromatography and/or cation exchange chromatography.

5. The production method according to claim 1, wherein the malignant tumor cells are not genetically engineered.

6. The production method according to claim 3, wherein the physiological buffer salt solution is selected from the group consisting of Hanks' balanced salt solution, Earle's balanced salt solution, and phosphate buffered saline.

7. The production method according to claim 1, wherein the malignant tumor cells are not genetically engineered.

8. The production method according to claim 2, wherein the malignant tumor cells are not genetically engineered.

9. The preparation method according to claim 3, wherein the malignant tumor cells are not genetically engineered.

* * * * *